(12) United States Patent
Florin et al.

(10) Patent No.: US 11,077,112 B2
(45) Date of Patent: Aug. 3, 2021

(54) FORMULATION AND TREATMENT METHODS

(71) Applicant: PRODRUGXTEND PTY LTD, East Brisbane (AU)

(72) Inventors: Timothy Florin, Woolloongabba (AU); Amirali Popat, Northgate (AU); Siddharth Jambhrunkar, South Australia (AU)

(73) Assignee: PRODRUGXTEND PTY LTD, East Brisbane (AU)

( * ) Notice: Subject to any disclaimer, the term of this patent is extended or adjusted under 35 U.S.C. 154(b) by 0 days.

(21) Appl. No.: 15/764,247

(22) PCT Filed: Sep. 29, 2016

(86) PCT No.: PCT/AU2016/050910
§ 371 (c)(1),
(2) Date: Mar. 28, 2018

(87) PCT Pub. No.: WO2017/054042
PCT Pub. Date: Apr. 6, 2017

(65) Prior Publication Data
US 2018/0235972 A1 Aug. 23, 2018

(30) Foreign Application Priority Data

Sep. 29, 2015 (AU) ................................ 2015903951
May 20, 2016 (AU) ................................ 2016901896

(51) Int. Cl.
*A61K 31/52* (2006.01)
*A61K 9/00* (2006.01)
*A61K 9/28* (2006.01)
*A61K 9/20* (2006.01)
*A61K 9/08* (2006.01)

(52) U.S. Cl.
CPC ............ *A61K 31/52* (2013.01); *A61K 9/0031* (2013.01); *A61K 9/0053* (2013.01); *A61K 9/08* (2013.01); *A61K 9/20* (2013.01); *A61K 9/2018* (2013.01); *A61K 9/2027* (2013.01); *A61K 9/2054* (2013.01); *A61K 9/2059* (2013.01); *A61K 9/28* (2013.01)

(58) Field of Classification Search
CPC ............ A61K 31/52; A61K 9/00; A61K 9/28
See application file for complete search history.

(56) References Cited

U.S. PATENT DOCUMENTS

| | | |
|---|---|---|
| 5,108,758 A | 4/1992 | Allwood et al. |
| 5,905,081 A | 5/1999 | Sandborn |
| 6,166,024 A * | 12/2000 | Sandborn ............ A61K 9/0031 514/263.36 |
| 6,277,412 B1 | 8/2001 | Otterbeck |
| 6,395,273 B1 | 5/2002 | Kink et al. |
| 6,432,667 B1 | 8/2002 | Valenzuela et al. |
| 2006/0009473 A1 | 1/2006 | Lerner et al. |
| 2008/0317666 A1 | 12/2008 | Fattal |
| 2013/0005749 A1 | 1/2013 | Florin et al. |
| 2014/0370105 A1 | 12/2014 | Rosenberger et al. |

FOREIGN PATENT DOCUMENTS

| | | |
|---|---|---|
| EP | 2098236 A1 | 9/2009 |
| EP | 2110130 A1 | 10/2009 |
| GB | 2494439 A | 3/2013 |
| WO | WO 9630021 A1 | 10/1996 |
| WO | 2002/041875 A2 | 10/2001 |
| WO | 2009/109356 A2 | 9/2009 |
| WO | WO 2017066619 A1 | 4/2017 |

OTHER PUBLICATIONS

Birmingham et al, "Autophagy controls Salmonella infection in response to damage to the Salmonella-containing vacuole."J Biol Chem. Apr. 21, 2006;281(16):11374-83.
Chourasia, et al., "Pharmaceutical approaches to colon targeted drug delivery systems." J Pharm. Pharmaceutical Sci, 2003, 6(1): 33-66.
Dervieux, et al., "Liquid chromatography-tandem mass spectrometry analysis of erythrocyte thiopurine nucleotides and effect of thiopurine methyltransferase gene variants on these metabolites in patients receiving azathioprine/6-mercaptopurine therapy." Clin Chem. Nov. 2005;51(11):2074-84.
Jharap et al., "Biotransformation of 6-thioguanine in inflammatory bowel disease patients: a comparison of oral and intravenous administration of 6-thioguanine." British Journal of Pharmacology, 2011, 163:722-731.
Kabeya et al., "LC3, a mammalian homologue of yeast Apg8p, is localized in autophagosome membranes after processing." EMBO J. Nov. 1, 2000;19(21):5720-8.
Kverka, "Safety and efficacy of the immunosuppressive agent 6-tioguanine in murine model of acute and chronic colititis." BMC Gastroenterology 2011, 11:47, 9 pages.
Parikh et al. "Suppression of p21Rac signaling and increased innate immunity mediate remission in Crohn's disease." Sci Transl Med. Apr. 23, 2014; 6(233):233ra53.
Poppe et al, "Azathioprine suppresses ezrin-radixin-moesin-dependent T cell-APC conjugation through inhibition of Vav guanosine exchange activity on Rac proteins." J Immunol. Jan. 1, 2006; 176(1):640-51.
Remington: The Science and Practice of Pharmacy, Loyd V. Allen, Jr (Ed), The Pharmaceutical Press, London, 22nd Edition, Sep. 2012.

(Continued)

*Primary Examiner* — Zohreh A Fay
(74) *Attorney, Agent, or Firm* — Casimir Jones, S.C.; Lisa V. Mueller

(57) ABSTRACT

The invention relates to pharmaceutical compositions comprising 6-thioguanidine (6-TG) wherein the composition is formulated for release of 6-TG in the distal intestine. Methods for treating a disease or condition of the distal ileum that responds to 6-TG wherein the 6-TG is released in the distal intestine are also disclosed.

16 Claims, 22 Drawing Sheets

(56) References Cited

OTHER PUBLICATIONS

Schellekens, "Translational Research Into Oral Colon-Specific Drug Delivery: From Laboratory to Clinic." Copyright © 2011.
St. Clair Jones, "Inflammatory bowel disease—drug treatment and its implications." Hospital Pharmacist, May 2006, 13: 161-166.
International Search Report and Written Opinion dated Oct. 31, 2016 for PCT/AU2016/050910, 10 pages.
European Search Report dated Apr. 8, 2019, European Application Application No. 16849949.9, 13 pages.

* cited by examiner

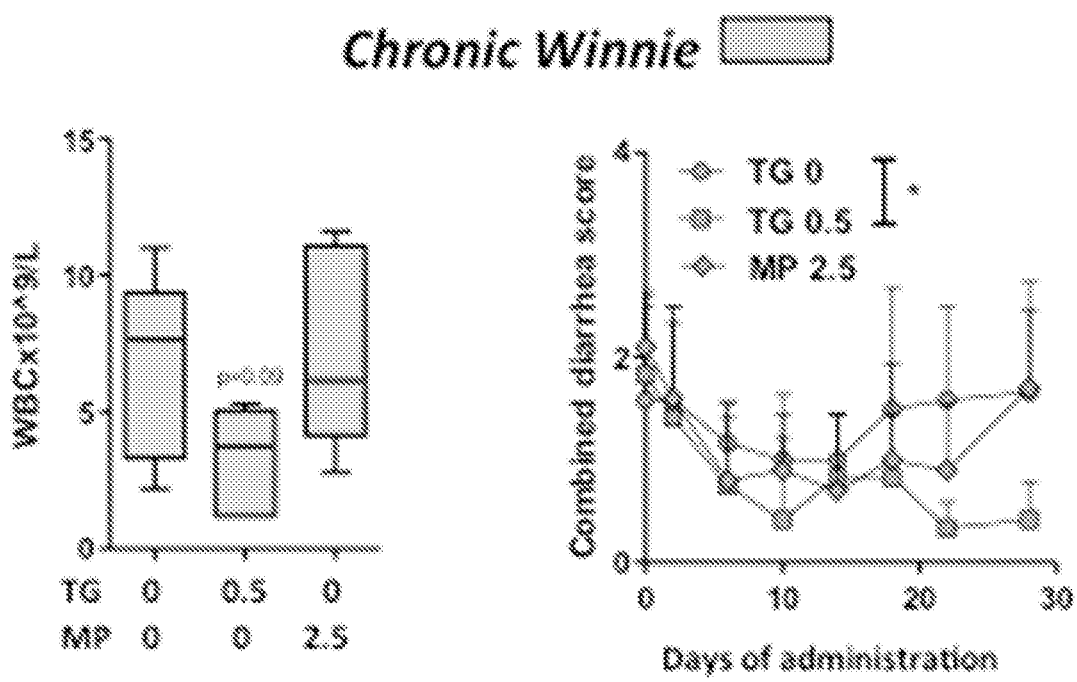
Figure 3A
Figure 3B
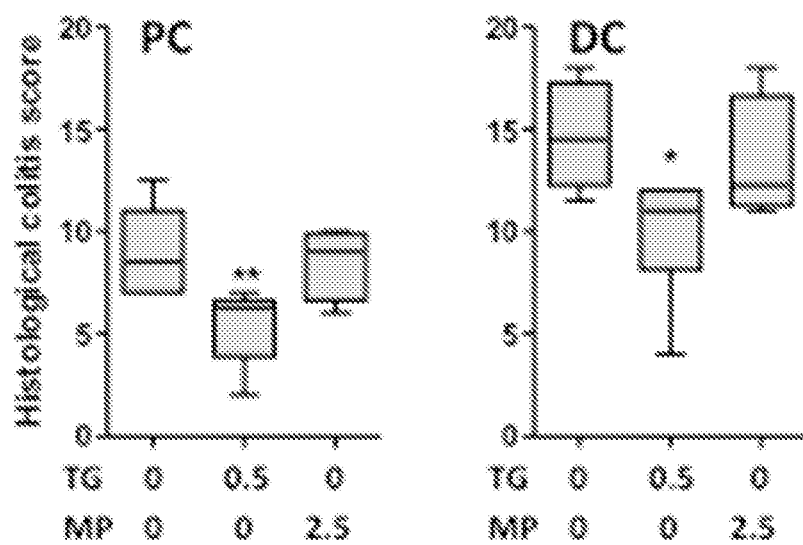
Figure 3C

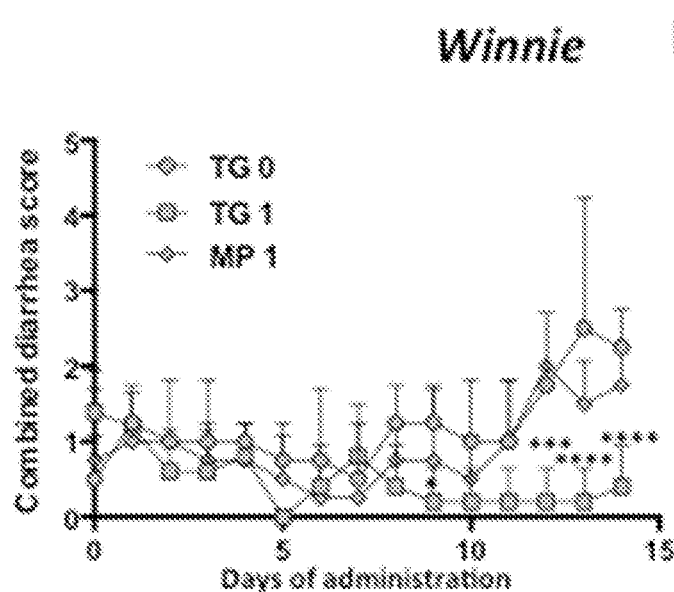
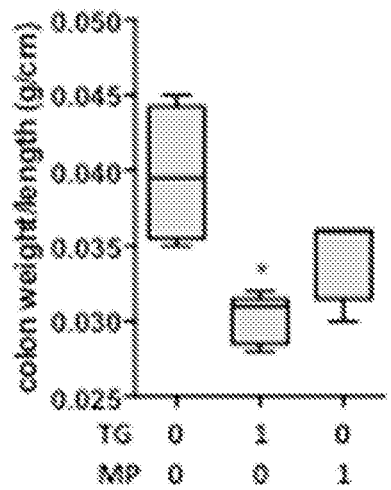
Figure 6A  Figure 6B
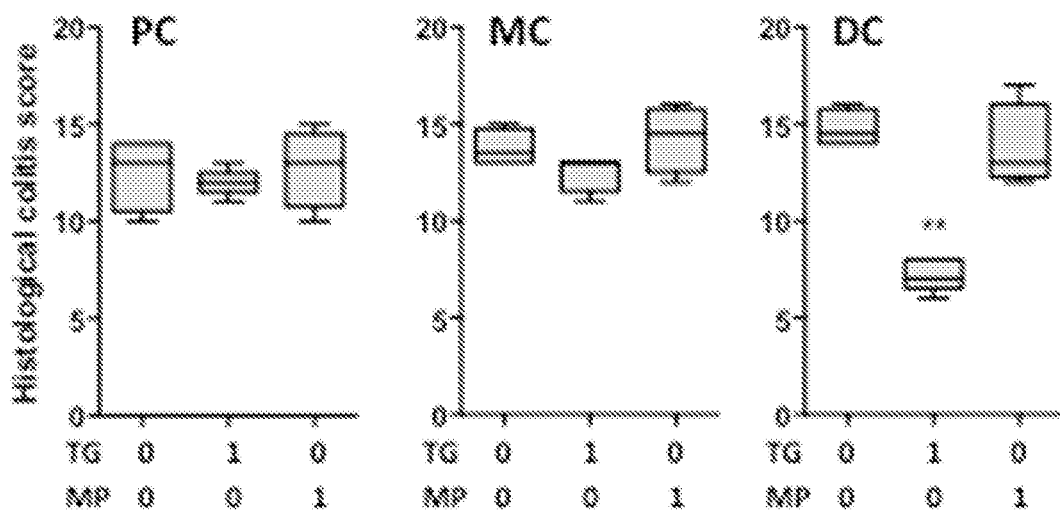
Figure 6C

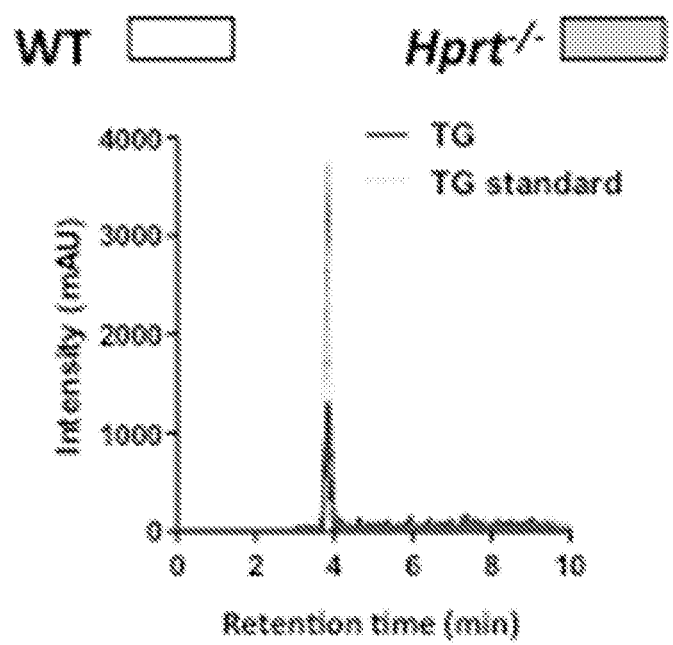
Figure 6E
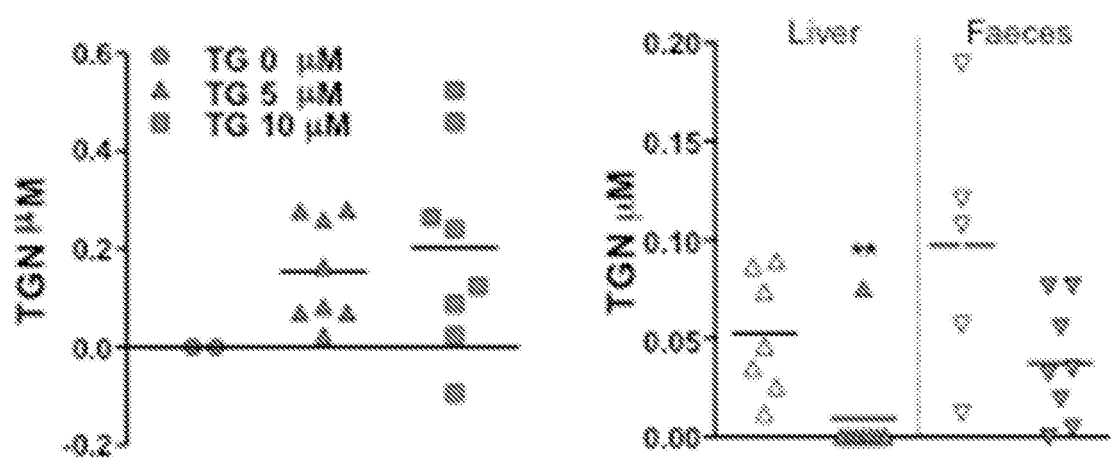
Figure 6F
Figure 6G

Figure 7AFigure 7B

Local TG is
metabolised by -
- commensal bacteria
- mucosal cells.

Epithelial/ mucosal TGN
induces autophagy & killing of
(translocated) bacteria

FORMULATION AND TREATMENT METHODS

FIELD OF THE INVENTION

This application is a 371 of PCT/AU2016/050910 filed on Sep. 29, 2016 which claims priority to Australian Provisional Application No. 2015903951 filed on Sep. 29, 2015 and Australian Provisional Application No. 2016901896 filed on May 20, 2016, the contents of which are incorporated herein by reference.

The present invention relates generally to novel formulations of 6-thioguanine (6-TG) and their use in improved treatment methods.

BACKGROUND OF THE INVENTION

Thiopurine compounds 6-mercaptopurine (6-MP; 3,7-dihydropurine-6-thione) and azathioprine (AZA; 6-(3-methyl-5-nitroimidazol-4-yl)sulfanyl-7H-purine) are prodrugs which are metabolized to form 6-thioguanosine-triphosphate (6-TGTP) as the principal active metabolite via the salvage pathway of purine metabolism. AZA and 6-MP are used in the treatment of a number of diseases and conditions, such as inflammatory conditions; cancers; autoimmune conditions; and post-transplant immunosuppression. These compounds are also used in therapy for inflammatory bowel disease (IBD) despite the long time-to-onset of clinical activity of typically three to four months, and the relatively fine line between the desired clinical end-point of controlled immunosuppression and the side-effect of leukopenia.

Conversion of AZA or 6-MP by some cells in the body, including liver cells and white blood cells, produces active metabolites in the form of thioguanine nucleotides (6-TGNs; principally 6-TGTP, and to a lesser extent 6-TGMP or 6-TGDP). This metabolic pathway is summarised diagrammatically in FIG. 1.

6-TGTP acts on activated circulating T-lymphocytes leading to proliferation arrest and then apoptosis. The reduction in gut-homing circulating immune cells then turns off the adaptive immune system's amplification of inflammation at the site of IBD. However, the metabolism of AZA/6-MP to thioguanine nucleotides (6TGNs) is rate limited by the enzyme inosine monophosphate dehydrogenase (IMPDH). The appearance of 6-TGNs from the metabolism of AZA/6-MP takes days, with a steady state taking at least about four weeks to achieve. The pharmacodynamic action, i.e., the clinical action, typically takes three to four months to achieve. Furthermore, methylated metabolites such as me6MP, me6MPr and meTIMP are also produced during the conversion of AZA and 6-MP. High levels of these methylated metabolites are associated with a number of undesirable side-effects, including hepatotoxicity, nausea, extreme fatigue, myalgia, pancreatitis, and myelosuppression (beyond that predicted from a 6-TGTP-induced immunosuppressive effect). These side-effects are serious in a large percentage of patients prescribed either 6-MP or AZA and this factor, along with the slow onset of action, limits the use of 6-MP and AZA.

According to current clinical practice, an alternative thiopurine compound, 6-thioguanine (6-TG; 2-amino-6,7-dihydro-3H-purine-6-thione), may be prescribed as an alternative in the situation when 6-MP or AZA therapy has been unsuccessful.

6-TG is converted to TGNs, but is not functionally equivalent to 6-MP or AZA therapy. With reference to FIG. 1, 6-TG is converted to 6-TGTP, the same principal active metabolite as 6-MP or AZA, but 6-TG is metabolised more directly by the enzyme hypoxanthine-guanine phosphoribosyltransferase (HPRT), i.e., the same principal active metabolite formed by metabolism of 6-MP or AZA, but the metabolic pathway is different. 6-TG is first converted to a monophosphate analogue (6-TGMP) by HPRT and is then converted via kinases to the active metabolite 6-TGTP. Fewer metabolic steps are required to convert 6-TG to the active drug, and the conversion of 6-TG is not rate-limited by the enzyme IMPDH. Therefore conversion of 6-TG to 6-TGTP is significantly faster than 6-MP or AZA and so a clinically faster onset of action is possible by using 6-TG. Furthermore, the less desirable methylated metabolites produced during metabolism of 6-MP or AZA are not produced when the body metabolises 6-TG.

Unfortunately, the faster onset of 6-TG treatment is strongly associated with serious hepatotoxic side-effects producing liver vascular disease comprising sinusoidal obstructive syndrome (SOS); veno-occlusive disease (VOD); or nodular regenerative hyperplasia (NRH). These vascular hepatotoxic side-effects are not significantly associated with 6-MP or AZA.

Studies indicated that mice receiving oral 6-TG exhibited vascular hepatotoxic side-effects associated with 6-TG. However, mice exhibited substantially less of these side-effects when orally administered the same total daily dose of 6-TG in two separate doses, indicating that the hepatic vascular toxicity is peak-concentration related (US 2013005749 A1). Dosage regimes for 6-TG were developed that provided systemic concentrations of active metabolite in an amount sufficient to induce effective treatment, but without providing a toxic level of the active metabolite in the liver. However, these forms of 6-TG administration still rely on a predominant hepatic conversion to the active metabolite where hepatotoxicity may be a consideration. Furthermore, since the systemic concentration of 6-TGTP acts on the circulating immune cells, this mechanism of action is slow and, more significantly, is also associated with immunosuppression (myelosuppression) resulting from destruction of white cells in the blood and bone marrow.

There is a need for improved therapies that overcome one or more of the drawbacks of the present therapies for inflammatory bowel disease.

SUMMARY OF THE INVENTION

It has now been discovered that a low dose of 6-TG, but not 6-MP results in a rapid local anti-inflammatory effect in the colon without significant immunosuppression. Furthermore, the targeted release provides a method of treatment of IBD which provides a faster mechanism of action that does not generate appreciable systemic concentrations of 6-TGN, and thus addresses the problem of the toxic side effects of 6-TG, namely vascular hepatotoxicity (such as SOS) and immunosuppression due to rapid anabolic metabolism of 6-TG.

This invention is predicated on the surprising discovery that there is a rapid and appreciable reduction in disease activity (inflammation) in Hprt$^{-/-}$ mice (i.e. mice lacking the key enzyme catalyzing the metabolism of 6-TG) in which colitis had been induced with dextran sodium sulphate (DSS) in the drinking water. This discovery was particularly unexpected as these mice lack the ability to form TGNs (the active metabolites) through the conventional metabolic route in the liver and leukocytes. However, formation of the active metabolite was discovered outside the generally understood mechanism. The magnitude of the reduction in disease activity was similar to that found in wild-type mice in which colitis had been induced with DSS. In comparison, there was no reduction in colitis over one month even with large doses of 6-MP in DSS induced colitis, reflecting the fast onset of action associated with administration of 6-TG compared to about 12 to 16 weeks for onset of action with 6-MP and AZA. The surprising finding that 6-TG effected treatment in the complete absence of host Hprt and absence of systemic 6-TGTP, implied that 6-TG is converted to 6-TGTP via HPRT in resident intestinal bacteria. In vitro incubation of representative gut bacteria *E. coli, Enterococcus faecalis* or *Bacteroides thetaiotamicron* with either 6-TG or 6-MP over 60 minutes confirmed that these bacteria could metabolise 6-TG to active metabolite 6-TGTP. Conversion of the related thiopurine, 6-MP, to 6-TGTP was considerably less over the same period consistent with rate-limiting IMPDH in the purine salvage pathway of bacteria.

When 6-TG is administered in an immediate release form (bolus dose) to IBD patients it is converted to 6-TGTP systemically by the liver and white blood cells. It is believed that 6-TGTP acts on circulating white blood cells (in particular, T-lymphocytes) thus mediating the beneficial immunomodulation to treat IBD. Surprisingly, in mice, it has been discovered that T- and B-lymphocytes are not required for 6-TG to ameliorate colitis. 6-TG can act therapeutically in a manner which is independent of the adaptive immune system. Without wishing to be bound by theory, it is believed that 6-TG is converted to the active metabolite 6-TGTP by luminal bacteria or the diseased mucosa at the site of inflammation without any appreciable systemic concentration.

These surprising findings have enabled the development of pharmaceutical compositions which release 6-TG in the region of the distal intestine, i.e. the distal ileum and colon. These new findings demonstrating local effect of 6-TG have enabled rectal enemas to be developed which are effective in treating diseased tissue of the colon directly at the site of inflammation. Moreover, these findings have also enabled the development of oral extended release formulations which are formulated to release 6-TG in the distal intestine at the site of inflammation. This targeted 6-TG administration is efficacious as the active metabolite is generated and released at the site of inflammation. Vascular hepatotoxicity and myelosuppression are greatly reduced or avoided as the colon is poorly absorptive and the therapeutic effect is largely through action of a local low dose of 6-TG on the distal intestine.

Accordingly, in one aspect the present invention advantageously provides a pharmaceutical composition comprising 6-thioguanidinr (6-TG) wherein the composition is formulated for release of 6-TG in the distal intestine.

In a further aspect the present invention advantageously provides a pharmaceutical composition comprising 6-TG and a pharmaceutically acceptable carrier, wherein the composition is formulated for enema administration.

In yet further aspect, the present invention provides a pharmaceutical composition formulated for oral administration comprising 6-TG and a pharmaceutically acceptable carrier, wherein the composition is formulated for release of 6-TG in the distal intestine.

In another aspect, the present invention advantageously provides a pharmaceutical composition formulated for oral administration comprising 6-TG and a pharmaceutically acceptable carrier, wherein the composition is formulated to release 6-TG at a rate of from 0.2 mg/hour to 1 mg/hour after approximately 12 hours from oral administration.

In a yet further aspect, the present invention provides a pharmaceutical composition comprising 6-TG wherein the composition is in a form suitable for oral administration and comprises, in admixture with 6-TG, a pharmaceutically acceptable carrier selected to provide for the extended release of 6-TG at a rate of from 0.2 mg/hour up to 1 mg/hour in the distal intestine over a period extending from approximately 12 hours up to between 24 and 36 hours following oral administration. In certain embodiments the composition further comprises an enteric coating.

In another aspect, the present invention provides a pharmaceutical composition comprising 6-TG formulated for oral administration, wherein at least 45% of the 6-TG is released in the colon.

In another aspect, the present invention advantageously provides a pharmaceutical composition according to the invention wherein the composition is for treating an inflammatory disease or condition of the distal ileum and/or colon responsive to 6-TG, for example inflammatory bowel disease.

In a further aspect, the present invention advantageously provides a method for treating a disease or condition of the distal ileum and/or colon that responds to 6-TG in an individual in need thereof, the method comprising administering 6-TG to the individual, wherein the 6-TG is released in the distal intestine. For example, systemic concentrations of 6-TG are substantially avoided. For example, the 6-TG is metabolized by luminal bacterial or diseased mucosa at a site of inflammation associated with the disease or condition. The method may comprise oral or enema administration. The method may comprise administration of a composition of the invention.

In a yet further aspect, the present invention provides a method according to the invention further comprising administering an additional active agent for treating a disease or condition responsive to 6-TG.

In yet another aspect, the present invention provides the use of 6-TG in the manufacture of a medicament, wherein the medicament is formulated to treat a disease or condition of the distal ileum and/or colon that responds to 6-TG by releasing the 6-TG in the distal intestine.

BRIEF DESCRIPTION OF THE DRAWINGS

FIG. 2A) Blinded scoring of histological colitis for proximal (PC) and distal colon (DC); FIG. 2B) Representative H&E for PC and DC of WT and Winnie treated with daily 6-TG 0 or 2.5 mg/kg; FIG. 2C) mRNA fold change normalized to ft-actin gene and to WT control of Tnf-α, Ifn-γ, Il-Ib, Il-17, Muc2. Box and whiskers plots of median, quartiles and range, N=4-6. Symbols: * versus WT TG 0 mg/kg; # versus Winnie 6-TG 0 mg/kg. Statistical analysis: Mann-Whitney non-parametric test. Scale bar=100 µm.

FIGS. 3A-3G shows data demonstrating that administration of a clinically relevant low dose of 6-TG over 28 days improved both spontaneous Winnie colitis, and chronic DSS induced colitis. FIGS. 3A-3C: Winnie mice were daily gavaged with either 6-TG 0, 0.5 or 6-MP 2.5 mg/kg/day for 28 days. FIG. 3A) Peripheral blood white cell count (WBC), FIG. 3B) Combined diarrhoea score one-way ANOVA P<0.05 at 28 days; FIG. 3C) Histological colitis scores for PC and DC in Winnie. FIGS. 3D-3G: WT mice were administered either water or 0.5% DSS in drinking water for 4 cycles (5 days on, then 7 days off for first 2 cycles and 9 days off for the last 2 cycles). The WT mice were also daily gavaged 6-TG 0 or 0.5 mg/kg for the last two cycles (28 days). FIG. 3D) peripheral blood white cell counts (WBC); FIG. 3E) Combined diarrhoea score, was significantly improved with treatment (two-way ANOVA P<0.05 at day 34, P<0.001 after day 40); FIG. 3F) colon weight; FIG. 3G) Histological colitis scores for PC and DC for WT mice with or without DSS or 6-TG.

FIGS. 4A and 4B: Acute administration of TG in Winnie and RaW ($Rag^{-/-}$×Winnie) mice daily gavaged 6-TG 0 or 2.5 mg/kg/day for up to 14 days. FIG. 4A) Histological colitis scores for PC and DC in Winnie (light grey bars) and RaW (dark bars); FIG. 4B) Representative H&E/Alcian blue staining for DC of Winnie and RaW mice treated with daily 6-TG 0 or 2.5 mg/kg for 12 days. Statistical analysis: Mann-Whitney non-parametric test. Symbols: * v Winnie 6-TG 0 mg/kg; # v RaW TG 0 mg/kg.

FIG. 5A) % change body weight over the last 2 cycles. Statistical analysis: one-way ANOVA with Dunn's multiple comparison; FIG. 5B) Disease activity indices (DAI) 2-way ANOVA P<0.001 from day 42; FIG. 5C) Colon weight/length ratio; FIG. 5D) Histological colitis scores for PC, MC (mid colon) and DC in $Hprt^{-/-}$ treated with or without DSS or 6-TG; FIG. 5E) Representative H&E from MC of $Hprt^{-/-}$ treated with 0.5% DSS, 6-TG 0 versus 0.5 mg/kg; FIG. 5F) Peripheral blood white cell counts and mesenteric lymph node (MLN) total cell number; FIG. 5G) CD3e+CD4+T lymphocyte, myeloid (CD3e-CD11b+) and dendritic cell (CD3-CD11c+MHCII+) numbers in MLN were not altered by 6-TG in $Hprt^{-/-}$ mice. N=2-8, from two to three experiments. Statistical analysis: Mann-Whitney non-parametric test. Symbols: * v $Hprt^{-/-}$ 6-TG 0 mg/kg; # v $Hprt^{-/-}$DSS 6-TG 0 mg/kg. Scale bar=100 µm.

FIGS. 6A-6G shows data demonstrating that daily administration of intrarectal 6-TG, but not 6-MP at 1 mg/Kg, effected a rapid local improvement in spontaneous colitis. FIG. 6A) Combined diarrhea score; FIG. 6B) Colon weight/length ratio: FIG. 6C) Blinded histological scoring of colitis for distal colon (DC), mid colon (MC) and proximal colon (PC) in Winnie mice. Gut representative bacteria converted 6-TG to thioguanine nucleotides (6-TGN). In vitro: FIG. 6D) Mean TGN (SEM) in *E. coli* (Gram negative), *Enterococcus faecalis* (Gram positive), *Bacteroides thetaiotamicron* (Gram negative anaerobe) cultures incubated with 1 mM 6-TG or 6-MP for up to 120 minutes, N=3-4; *vs T0, # vs T30, & vs T60; FIG. 6E) LC-MS measurement of 6-TGN after conversion to 6-TG (5 µM 6-TG standard in red); FIG. 6F) Scatter plots, mean 6-TGN at 6 hours in $Hprt^{-/-}$ mouse faeces incubated with 0, 5 or 10 µM 6-TG. In vivo: FIG. 6G) WT and $Hprt^{-/-}$ mice gavaged 5 mg/kg 6-TG: scatter plots, mean 6-TGN in liver and faeces. Statistical analysis: Mann-Whitney non-parametric test. Symbols: * vs WT mice.

FIGS. 7A-7F shows data demonstrating that 6-TG promotes autophagy. 6-TG administration enhanced autophagy in vitro: Western blots for LC3-I, LC3-II and β-actin FIG. 7A) HeLa cells treated with DMSO 0.1% (vehicle control), 6-TG (10 or 100 µM) or both plus Pepstatin A and E64D (PE) for 16 h; FIG. 7B) HT29, HCT 116 and HepG2 cells line treated with DMSO 0.1% or 6-TG 50 µM for 16 h; FIG. 7C) LC3-I: LC3-II ratio in RAW cells with and without 6-TG; Bacterial replication assay: FIG. 7D) HeLa cells were pretreated overnight with vehicle control (DMSO) or 6-TG (10, 50 and 100 µM) and treatment was then reapplied with SL1344 infection: SL1344 Lux replication readings at 12 h post infection; 6-TG did not alter bacterial growth (OD 600 absorbance) over that time period. N=4-8 experiments; FIG. 7E) Fluorescence microscopy quantification and image of autophagosome encapsulation of SL1344 bacteria with or without treatment with 6-TG 50 µM in HeLa cells. Blue-DAPI nuclear stain; red-free *Salmonella*, green-LC3 autophagosome encapsulation of bacteria. Bars, mean±SD, N=3 Statistical analysis: unpaired t test *P<0.05. The 6-TG effect on autophagy was Hprt-dependent: FIG. 7F) LC3-II to β-actin ratio quantification. WT and $Hprt^{-/-}$ derived primary murine fibroblasts treated with DMSO 0.1% or 50 µM 6-TG for 16 h. N=5-6. Western blot image. Statistical analysis: Mann-Whitney non-parametric test: * P<0.05 WT 6-TG 50 v 0 µM; ## P<0.01 6-TG 50 µM $Hprt^{-/-}$ v WT 6-TG 50 µM.

DETAILED DESCRIPTION OF THE INVENTION

Definitions

Figure 1:
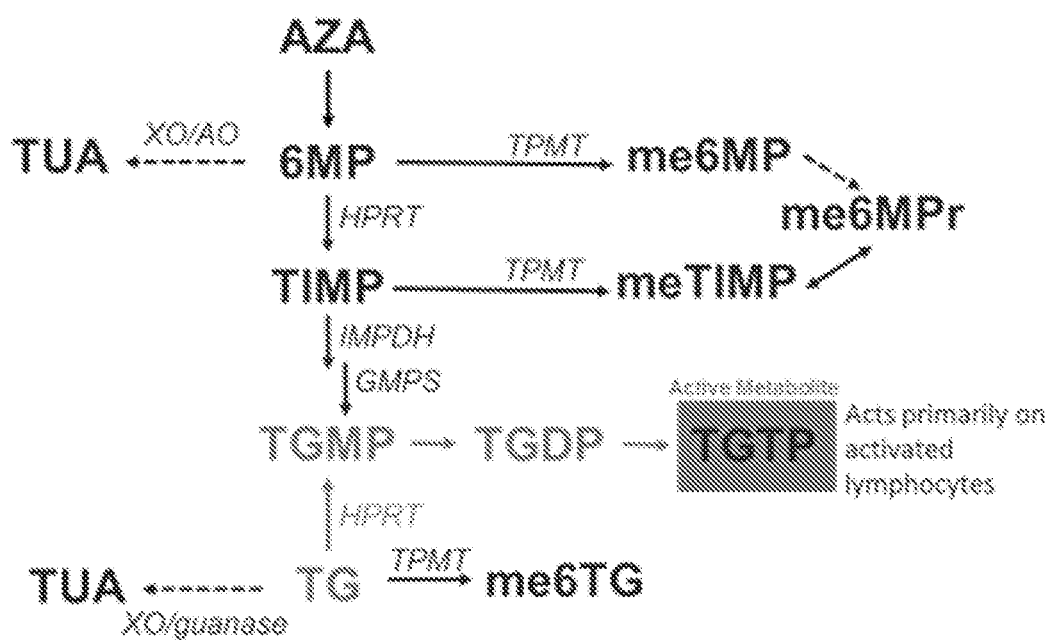
FIG. 1 is a schematic diagram illustrating the metabolic pathway of the thiopurines.
Thiopurines: AZA: azathioprine; 6MP: 6-mercaptopurine; TG: 6-thioguanine; Thiopurine nucleotides: TGMP: thioguanosine monophosphate; TGDP: thioguanosine diphosphate; TGTP: thioguanosine triphosphate; Anabolic enzymes & metabolites: IMPDH: inosinemonophosphate dehydrogenase; GMPS: guanosinemonophosphate synthase; TIMP: thioinosine monophosphate; ITPA: inosine triphosphatase; HPRT: hypoxanthine guanine phosphoribosyl transferase.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, the term "about" refers to a quantity, level, concentration, value, size, or amount that varies by as much as 10% or even as much as 9%, 8%, 7%, 6%, 5%, 4%, 3%, 2%, 1%, to a reference quantity, level, concentration, value, size, or amount.

Throughout this specification, unless the context requires otherwise, the words "comprise," "comprises" and "comprising" will be understood to imply the inclusion of a stated step or element or group of steps or elements but not the exclusion of any other step or element or group of steps or elements.

As used herein the term "distal intestine" refers to the section of intestine comprising the distal ileum and colon. In some embodiments the relevant section of the distal intestine is the colon.

As used herein, the term "colon" refers to the large bowel or large intestine minus the rectum. That is, the term "colon" refers to the section of intestine consisting of the caecum, ascending colon, transverse colon, descending colon and sigmoid colon.

As used herein, the phrase "diseases or conditions of the distal ileum and/or colon that respond to 6-TG", "diseases or conditions of the distal intestine that respond to 6-TG" and similar refers to any disease or condition of the distal ileum or colon which can be treated by 6-TG, including treatment of any symptom of the disease or condition. Preferably the disease or condition is an inflammatory disease or condition. Examples of such inflammatory diseases or conditions include ulcerative colitis, Crohn's disease and IBD-U (IBD-Undifferentiated).

When used herein, the phrase "inflammatory bowel disease" is a condition that affects the distal ileum and/or colon and includes ulcerative colitis, Crohn's disease and IBD-U (IBD-Undifferentiated).

The term "extended-release formulation" refers to a formulation that is converted or degraded or metabolised into, or provides a source of, the active component that it contains (e.g., 6-TG) over an extended period of time. Such formulations may also be referred to in the art as slow release, or sustained release formulations.

The term "extended release" refers to release of the active pharmaceutical ingredient (6-TG) from a pharmaceutical formulation over an extended period of time, thus providing continuous local delivery of 6-TG as the formulation passes through the distal intestine. In some embodiments the extended release of 6-TG has substantially zero order kinetics.

The terms "individual", "patient" and "subject" are used interchangeably herein to refer to individuals of human or other animal origin and includes any individual it is desired to examine or treat using the methods of the invention. However, it will be understood that these terms do not imply that symptoms are present. Suitable animals that fall within the scope of the invention include, but are not restricted to, humans, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes, birds, reptiles).

The phrase "6-TG side-effects" and similar expressions refers to the adverse or undesirable side-effects caused by a 6-TG metabolite thereof, including 6-TGTP (and/or related metabolites), including but not limited to vascular hepatotoxicity, including sinusoidal obstructive syndrome (SOS), veno-occlusive disease (VOD) and nodular regenerative hyperplasia (NRH); and immunosuppression or myelosuppression.

By "pharmaceutically acceptable excipient, carrier or diluent" is meant a solid or liquid filler, diluent or encapsulating substance that can be safely used in topical or systemic administration.

The terms "treat", "treating" or "treatment" as used herein cover the treatment of a disease or condition responsive to 6-TG in an individual having the disease or condition, and includes: inhibiting the disease or condition, i.e., arresting its development; relieving the disease or condition, i.e., causing regression of the disease or condition; or relieving the symptoms resulting from the disease or condition, i.e., relieving pain or inflammation without addressing the underlying disease or condition.

The present invention arises from the discoveries that 6-TG can act locally and rapidly at sites of inflammation, and be converted to the active metabolite 6-TGTP by the luminal bacteria without any appreciable systemic concentration. It is also believed that diseased mucosa or epithelial and resident white cells in the lining of the colon and/or distal ileum may be implicated in conversion of the 6-TG to 6-TGTP. The beneficial effect of 6-TG can be independent of T-lymphocytes. As the active metabolite is generated in the vicinity of the site of inflammation, this permits a more rapid therapeutic action than a protocol relying on systemic metabolism. This also addresses the problem of the toxic side effects of 6-TG such as vascular hepatotoxicity and immunosuppression. Based on the surprising discovery that 6-TG works well in treating colitis in the HPRT-deficient host, therapeutic protocols have been developed for more rapid treatment of diseases or conditions of the distal ileum and/or colon that respond to 6-TG without appreciable systemic concentration and reduced or no adverse 6-TG side-effects compared to conventional 6-TG therapy.

It has further been demonstrated that intra-rectal administration of 6-TG ameliorated spontaneous colitis within 14 days in the distal colon. There was no improvement in colitis in mid-colon or proximal colon indicating that the beneficial effect of 6-TG was local. Intra-rectal administration of 6-MP did not provide any significant improvement in colitis, demonstrating the lack of functional equivalence of 6-TG and 6-MP/AZA. Local delivery of 6-TG to sites of intestinal inflammation in IBD thus provides significant advantages over current immunomodulating therapies.

Without being bound by the theory, it is believed that 6-TG is metabolized by intestinal bacteria and/or by mucosal metabolism. The 6-TG is converted to 6-TGN. The 6-TGN itself do not exist outside of the cell. However, it is believed that translocating commensal or pathogenic bacteria in IBD are phagocytosed by intestinal epithelial cells and immune cells. The mucosal barrier, which would otherwise prevent significant translocation of bacteria, is damaged in IBD. Autophagy of the bacteria in the intracytoplasmic autophagosomes is increased by 6-TGN which leads to increased bacterial clearance by the epithelial cells. It is also believed that bacterially derived metabolites of 6-TG, in particular 6-TGTP, will be released by the bacteria which are killed by the intestinal epithelial and immune cells that line the distal ileum and colon. 6-TG is also converted by HPRT in the mucosa catalyzing addition of a ribosyl-phosphate to form 6-TGMP which is then converted intracellularly by thioguanosine kinases to 6-TGDP and 6-TGTP. This can be followed by catabolism by phosphatase and phosphorylase to 6-thioguanosine (6-TGr) and thence to 6-TG. Direct conversion of 6-thioguanosine (6-TGr) by a 6-TGr kinase to 6-TGMP may also occur.

Accordingly, the present invention provides a composition comprising 6-TG wherein the composition is formulated for release of 6-TG in the distal intestine, preferably the colon. Suitably the composition is a pharmaceutical composition. Suitably, the composition is formulated to release 6-TG substantially in the distal intestine. Suitably, the composition is formulated for extended release of 6-TG in the distal intestine. Suitably, the composition releases at least 45% of the 6-TG in the distal intestine. In some embodiments, the section of the distal intestine is the colon. Suitably, the composition is for treating a disease or condition of the distal ileum and/or colon responsive to 6-TG. Suitably, the composition is for treating IBD, e.g. ulcerative colitis, Crohn's disease or IBD-U. In some embodiments, the compositions may be used for treating microscopic colitides; e.g., lymphocytic (entero)colitis and collagenous (entero)colitis.

Suitably, the composition is formulated for oral administration or for enema administration. Preferably the composition is formulated for oral administration.

Suitably, the composition is an oral composition. Suitably, an oral composition is in an extended release form and comprises an extended-release formulation of 6-TG. The composition may be a pharmaceutical composition comprising 6-TG and a pharmaceutically acceptable carrier suitable for providing extended release of 6-TG.

Figure 11:
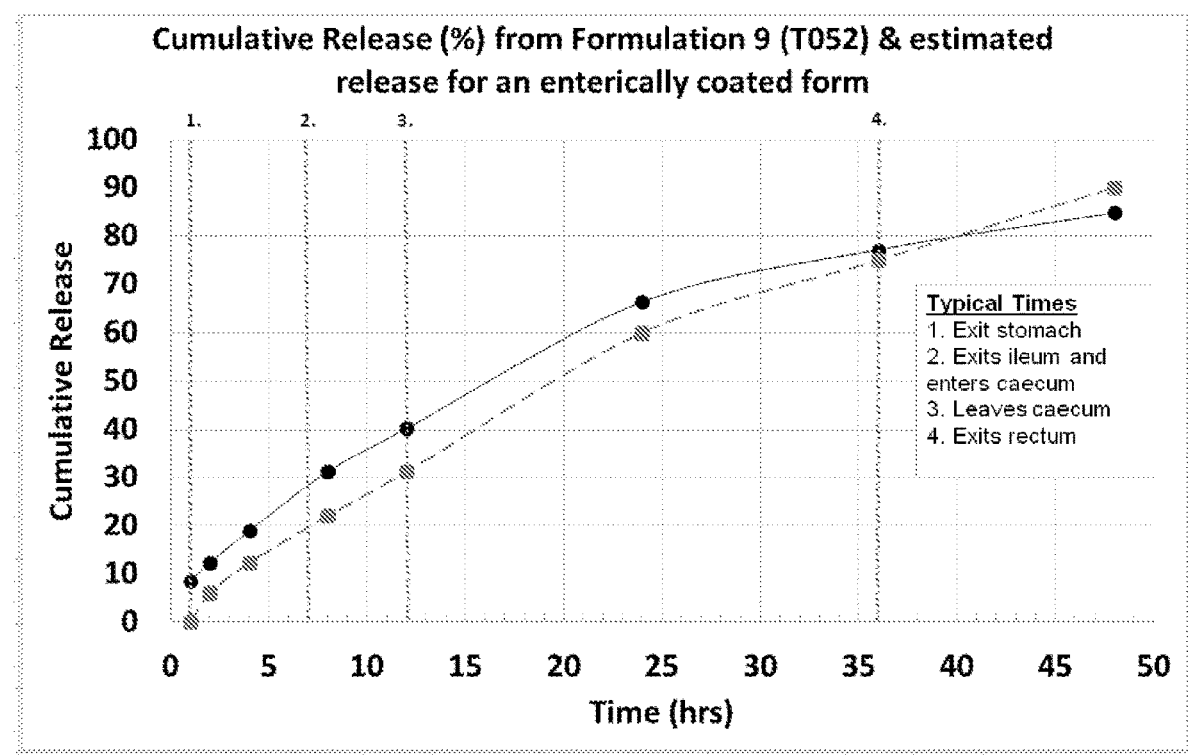
FIG. 11 is a graphical representation of the percentage cumulative release from Formulation 9 (T052) over 48 hours (solid line), together with an estimated percentage cumulative release for an enterically coated version of Formulation 9 over the same period (broken line).

The transit time of an oral composition from mouth to anus will vary considerably from individual to individual, and many parameters such as age, solid or liquid food intake, diet, weight, sex, health, disease state of gut, etc., will impinge on the actual transit time. Not all ingested material transits at the same rate, so that typically transit is measured as 50% clearance of oral markers that are ingested at the one time. The transit time from mouth to entry into duodenum typically varies from approximately 30 minutes to 90 minutes. The average time for transit through the small intestine from duodenum to entry into caecum is approximately 2-6 hours. The typical transit time from mouth to caecum is considered to be approximately 4-8 hours. The transit time through the colon (from caecum to anus) is approximately 12 to 36 hours). The typical transit time from mouth to anus is thus considered to be approximately 36 hours, although this may vary widely. Typical transit times may vary from about 20 hours to about 48 hours. Suitably, the oral composition is formulated to provide extended release of 6-TG after approximately 12 hours from oral administration. The release profile of exemplary oral formulations according to the invention is illustrated in FIG. 11.

Suitably, the oral composition is formulated to release 6-TG at a rate of from 0.2 mg/hour to 1 mg/hour after approximately 12 hours from oral administration. Without being bound by theory, it is believed that after 12 hours have elapsed after administration of an extended release oral formulation, the formulation will have entered the colon where it will release 6-TG as it continues to pass through the reminder of the distal intestine. In some embodiments, the formulation will provide approximately zero order kinetics of 6-TG release Suitably, the composition is formulated to release 6-TG at a rate of at least 0.2 mg/hour from 12 to 48 hours after oral administration. Suitably, the composition is formulated to release 6-TG at a rate of from 0.2 mg/hour to 5 mg/hour from 12 to 48 hours after oral administration. Suitably the release rate is at pH 6 to about pH 7.5. Suitably, the composition is formulated to release 6-TG at from about pH 6 to about pH 7.5. Suitably the formulation does not release 6-TG at pH<5.

In one aspect, the present invention provides a pharmaceutical composition comprising 6-TG wherein the composition is in a form suitable for oral administration and comprises, in admixture with the 6-TG, a pharmaceutically acceptable carrier selected to provide for the extended release of the 6-TG over a period extending from about 8 hours following oral administration. Preferably, the present invention provides a pharmaceutical composition comprising 6-TG wherein the composition is in a form suitable for oral administration and comprises, in admixture with the 6-TG, a pharmaceutically acceptable carrier selected to provide for the extended release of the 6-TG over a period extending from about 12 hours following oral administration. Preferably the release is substantially in the colon. Suitably, the composition provides for extended release over a period extending from 8 hours, 10 hours or 12 hours up to, for example, 18, 24, 30, 36, 40 or 48 hours following oral administration. Suitably the composition provides for extended release at a pH range of 6 to 7.5. Suitably, the composition is formulated to release 6-TG at a rate of from 0.2-0.4 mg/hour; 0.4-0.6 mg/hour, 0.4-0.8 mg/hour; 0.2-0.6 mg/hour; 0.2-1.0 mg/hour; 0.4-1.0 mg/hour; 0.2-1.5 mg/hour; 0.2-2 mg/hour; 0.2-2 mg/hour; or approximately 0.2, 0.3, 0.4, 0.5, 0.6, 0.7, 0.8, 1.0, 1.2, 1.5 or 2 mg/hour over a period extending from 12 hours. In one embodiment, the composition releases 6-TG at a rate of 0.28-0.4 mg/hour from 12 to 48 hours. It will be appreciated that the time end point may be egress of the formulation residue from the gut.

In some embodiments, an oral formulation of the invention releases 6-TG in a controlled manner and attains release of about 80% of 6-TG content by the end of 24 hours from oral administration.

In one embodiment, the composition is an enema composition. The enema composition may be a pharmaceutical composition comprising 6-TG and at least one pharmaceutically acceptable carrier. Suitably, an enema composition may be in the form of a solution or a suspension. Suitably the enema composition is useful for treating an inflammatory disease or condition of the colon, particularly the descending colon and/or sigmoid colon.

In a further aspect, the present invention provides a pharmaceutical composition comprising 6-TG and at least one pharmaceutically acceptable carrier adapted for enema administration.

In one embodiment, the method for treating an inflammatory disease or condition of the distal ileum and/or colon that responds to 6-TG in an individual in need thereof, the method comprising administering 6-TG to the individual, wherein the 6-TG is released in the distal intestine is inflammatory bowel disease (IBD). Preferably the 6-TG is released in the colon. Examples of forms of IBD include ulcerative colitis, Crohn's disease, and IBD-U. Suitably, the 6-TG is converted to active drug in the distal ileum or colon by luminal bacteria or diseased mucosa. Suitably, systemic concentrations of 6-TG are reduced, or avoided. Suitably, this method avoids or at least substantially reduces undesirable 6-TG side-effects, including vascular hepatotoxicity such as SOS, and myelosuppression, observed when hepatic portal or systemic concentrations of active or related metabolites are generated. In some embodiments, the method comprises oral or enema administration of 6-TG.

In some embodiments, the method comprises oral administration. Suitably, the method comprises administering a composition comprising an extended-release formulation of 6-TG, for example the method may comprise administering a composition of the present invention.

In some embodiments, the method comprises enema administration. Suitably, the method comprises administering an enema composition comprising 6-TG, for example the method may comprise administering a composition of the present invention. Suitably, the enema composition is in the form of a solution or a suspension. Suitably the method is for treating an inflammatory disease or condition of the colon, preferably the descending colon and/or sigmoid colon.

In some embodiments, the method further comprises administration of another active agent in addition to 6-TG for treating a disease or condition responsive to 6-TG, including but not limited to an active agent selected from the group consisting of: mesalazine (or 5-aminosalicylic acid), balsalazide, sulfasalazine, a corticosteroid, a cyclosporine compound, an anti-TNF-α compound. The additional active agent may be administered in the same composition or compositions, or in a different composition or composition to the composition(s) comprising 6-TG. The additional active agent may be administered at the same time or at a different time to the composition(s) comprising 6-TG. The present invention indicates combinations, kits or commercial packages comprising the 6-TG composition and a composition comprising the additional active agent. Such kits or commercial packages may include instructions for use. In some cases it may be appropriate to provide a composition comprising 6-TG and the other active agent. In some embodiments the composition does not comprise 6-MP or AZA. In some embodiments the composition comprises 6-TG as the sole active pharmaceutical ingredient.

Formulation and Administration Routes

The compositions of the present invention or the compositions used in the methods of the present invention may be formulated and administered using methods known in the art. Techniques for formulation and administration may be found in *Remington: The Science and Practice of Pharmacy*, Loyd V. Allen, Jr (Ed), The Pharmaceutical Press, London, 22$^{nd}$ Edition, September 2012.

The compositions may comprise at least one pharmaceutically acceptable excipient, carrier and/or diluent, including those that impart the desired consistency, strength, viscosity, texture and appearance. The compositions should also have the required shelf life in accordance with the International Conference on Harmonisation issued by the US Food and Drug Administration.

The compositions may, for example, be formulated readily using a pharmaceutically acceptable excipient, carrier and/or diluent, including those well known in the art, into dosages suitable for administration. Such excipients, diluents and carriers enable the compositions to be formulated into dosage forms such as tablets, pills, capsules, and the like, for oral administration to an individual. Such excipients, diluents and carriers enable the compositions to be formulated into enema dosage forms such as solutions and suspensions and the like for administration to an individual. Acceptable excipients, diluents and carriers are well known to those skilled in the art and include, but are not restricted to, saline, pyrogen-free or sterile water, sugars, sugar alcohols, starches, cellulose and its derivatives, gelatine, talc, colloidal silica, magnesium stearate, calcium sulphate, vegetable oils, synthetic oils, polyols, phosphate buffered solutions, and emulsifiers.

Pharmaceutical formulations for oral administration can be obtained by combining 6-TG with solid carriers, optionally grinding a resulting mixture, and processing the mixture of granules, after adding suitable auxiliaries, if desired, to obtain tablets or dragee cores. Suitable carriers are, in particular, fillers such as sugars or sugar alcohols, including lactose and mannitol; cellulose preparations such as, for example, starch, gum tragacanth, hydroxypropylmethylcellulose, and/or polyvinylpyrrolidone (PVP) and its derivatives. If desired, disintegrating agents may be added, such as starch, cross-linked polyvinyl pyrrolidone, agar, or alginic acid or a salt thereof such as sodium alginate. Such compositions may be prepared by any one of the methods of pharmacy but all methods include the step of bringing into associate 6-TG with the carrier which constitutes one or more necessary ingredients. In general, the pharmaceutical compositions of the present invention may be manufactured in a manner that is itself known, e.g., by means of conventional mixing, dissolving, granulating, dragee-making, emulsifying, encapsulating, entrapping or lyophilising processes. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterise different combinations of active compound doses.

Oral formulations may be administered in push-fit capsules made of gelatine, as well as soft, sealed capsules made of gelatine and a plasticiser, such as glycerol or sorbitol. The push-fit capsules can contain the active ingredients in admixture with filler such as lactose, binders such as starches, and/or lubricants such as talc or magnesium stearate and, optionally, stabilisers. In soft capsules, the active compounds may be dissolved or suspended in suitable liquids. In addition, stabilisers may be added.

Enema Formulations

In some aspects and embodiments, the compositions of the present invention are formulated for administration as an enema.

The present invention provides a composition comprising an enema formulation of 6-TG. Also provided is a method for treating an inflammatory disease or condition of the distal intestine, preferably the distal colon, that responds to 6-TG in an individual in need thereof, the method comprising administering to the individual an enema composition of the present invention comprising a formulation of 6-TG.

In some embodiments, the enema formulation comprises 6-TG and at least one pharmaceutically acceptable excipient.

A 6-TG composition for enema administration may be formulated, for example, as a solution or a suspension.

In some embodiments the 6-TG enema composition is a solution. In some embodiments the enema composition comprises 1 mg/100 mL to 100 mg/100 mL of 6-TG. In one embodiment, the 6-TG composition is a solution comprising about 10 mg/100 mL to 100 mg/100 mL of 6-TG, for example 10 mg/100 mL to 30 mg/100 mL; e.g. about 20 mg/mL 6-TG. In another embodiment, the 6-TG composition is a solution comprising 70 mg/100 mL to 90 mg/100 mL 6-TG, for example about 80 mg/100 mL 6-TG.

In some embodiments the 6-TG enema composition is a suspension. In some embodiments the enema suspension composition comprises 10 to 100 mg/100 mL of 6-TG. In another embodiment, the 6-TG composition is a suspension comprising 10 to 30 mg/100 mL of 6-TG, for example about 20 mg/mL of 6-TG. In another embodiment, the 6-TG composition is a suspension comprising 70 to 90 mg/100 mL 6-TG, for example about 80 mg/mL 6-TG.

In some embodiments an enema composition is administered as a daily unit dose. In some embodiments, the daily enema dose is 2 mg to 200 mg, preferably 5 mg to 50 mg. In some embodiments the daily enema dose is 0.04 to 4 mg/Kg, preferably 0.1 to 1 mg/Kg. In some embodiments a 100 mL enema formulation comprises 2 to 200 mg %, preferably 5 to 50 mg %. In some other embodiments, a 60 mL enema formulation comprises 3.3 to 330 mg %, preferably 8.3 to 830 mg %.

Enema formulations may be prepared by techniques known in the art. Suitable excipients, diluents and/or carriers for enema formulations are known in the art and include solvents, solubilising agents, pH modifiers, stabilisers and viscosity modifiers. Examples of diluents and/or carriers include water, propylene glycol, and aqueous propylene glycol.

In some embodiments, a solution enema formulation comprises 6-TG and one or more solubilizing agents. Examples of solubilizing agents include sodium hydroxide and methyl-β-cyclodextrin (Me-β-CD). In a particular embodiment a solution enema formulation comprises 6-TG, sodium hydroxide and methyl-β-cyclodextrin. In some embodiments, the solution enema comprises methyl-β-cyclodextrin in an amount up to 0.4% w/v. In some embodiments the ratio of methyl-β-cyclodextrin to 6-TG is 8:1 to 16:1.

In preferred embodiments the enema formulation further comprises one or more preservatives. Examples of preservatives include benzalkonium chloride and disodium edetate (EDTA).

Oral Extended-Release Formulations

The present invention provides a composition comprising an extended-release oral formulation of 6-TG. Also provided is a method for treating a disease or condition that responds to 6-TG in an individual in need thereof, the method comprising administering to the individual an oral composition of the present invention comprising an extended-release formulation of 6-TG.

The present invention provides a pharmaceutical composition formulated for oral administration comprising 6-TG and a pharmaceutically acceptable carrier, wherein the composition is formulated to release 6-TG at a rate of up to 1 mg/hour after 12 hours from oral administration.

There is also provided a pharmaceutical composition comprising 6-TG wherein the composition is in a form suitable for oral administration, preferably a tablet, and comprises, in admixture with 6-TG, a pharmaceutically acceptable carrier selected to provide for the extended release of 6-TG at a rate of from 0.2 mg/hour up to 1 mg/hour in the distal intestine over a period extending from 12 hours up to between 24 and 36 hours following oral administration.

As used herein, the term "extended-release formulation" refers to a formulation that is gradually converted or degraded or metabolized into, releases, or provides a source of, the pro-drug, drug, or active component that it contains (e.g., 6-TG) over an extended period of time.

In some embodiments, the extended-release formulation provides a release of 6-TG in the distal intestine at a release rate of from 0.2 mg/hour; for example from 0.2 mg/hour to 5 mg/hour; 0.2 mg/hour to 4 mg/hour; 0.2 mg/hour to 3 mg/hour; 0.2 mg/hour to 2.5 mg/hour; 0.2 mg/hour to 2 mg/hour; or from 0.2 mg/hour to 1 mg/hour. Preferably the release of 6-TG is substantially in the colon. In some embodiments, the release rate is from 12 to 24 hours, 12 to 36 hours or 12 to 48 hours, or from 12 hours until egress of the formulation from the gut. In some embodiments the release rate is from 8 or from 10 hours. In some embodiments, the release is at a rate of 0.2-0.4 mg/hour; 0.2-0.6 mg/hour; 0.25-0.4 mg/hour; 0.4-0.6 mg/hour; 0.4-0.8 mg/hour; or approximately 0.5 mg/hour. In some embodiments the release of 6-TG from the extended release formulation commences approximately 12 hours after oral administration. In some embodiments, the 6-TG extended release commences after dissolution of an enteric coating. In some embodiments, at least 45% of the 6-TG is released after 12 hours. In some embodiments, at least 45% of the 6-TG is released in the colon after 12 hours from oral administration. In some embodiments the release of 6-TG from the extended release formulation commences approximately 10-12 hours after oral administration.

In preferred embodiments, the extended-release formulation provides approximately zero order kinetics of 6-TG release (i.e., a linear delivery with respect to the time of extended release). Suitably, the extended-release formulation provides substantially zero order kinetics of 6-TG release from approximately 12 hours after oral administration. Suitably, the extended release formulation provides substantially zero order kinetics of 6-TG release from approximately 12 hours after oral administration wherein the substantially zero order release is maintained for at least a further 12 hours, or at least a further 18 or 24 hours It will be appreciated that the time end point may be egress of the formulation residue from the gut. In some embodiments, suitably the extended release formulation provides chronotropic release after the oral formulation has left the stomach.

Suitably, the extended-release oral formulations of the present invention are formulated so as to release or provide 6-TG to the distal intestine, preferably the colon. In illustrative embodiments, the formulation releases or provides the 6-TG to the distal intestine over a period extending from approximately 12 hours to 48 hours, or any period in between. In illustrative embodiments, the period is from 12 hours to 18 hours; or from 12 hours to 24 hours; or from 12 hours to 36 hours.

In some embodiments the oral formulation provides a 6-TG release of at least 45% of the total 6-TG in the distal intestine, preferably the colon. In some embodiments the oral formulation provides a 6-TG release of at least 50%, 55%, 60%, 65%, 70%, 75%, 80%, 85%, 90% or 95% of the total 6-TG in the distal intestine, preferably the colon. In some embodiments the oral formulation provides a 6-TG release of at least 35% of the total 6-TG in the distal intestine, and preferably in the colon.

In some embodiments, the oral formulation provides a 6-TG release of greater than 0.2 mg/hour after 12 hours from administration.

In some embodiments, the oral formulation provides a 6-TG release of at least 45% of the total 6-TG from 12 to 48 hours from administration.

In some embodiments, the oral formulation provides a 6-TG release of at least 45% of the total 6-TG at a rate of about 0.2 mg/hour from 12 to 48 hours from administration.

Suitably, the composition comprising the extended-release formulation of 6-TG comprises 6-TG, polymer and excipients sufficient to enable 6-TG release into the distal intestine or colon at the desired rate of release. In some embodiments, the oral composition includes a film coating, or an enteric coat, to prevent disintegration of the composition in the stomach. In some embodiments, the oral composition includes a film coating, or an enteric coat, to reduce or substantially prevent release of 6-TG prior to reaching the colon.

The extended release formulations may include suitable fillers, for example lactose, sucrose, glucose, mannitol, sorbitol, calcium carbonate, starch, dextrin, cyclodextrin, calcium sulphate dehydrate (or hydrate), tricalcium phosphate, or microcrystalline cellulose. Particular examples of fillers are lactose, corn starch, and mannitol.

The formulation may include an extended release agent which may be selected from, for example wax and its derivatives, hydrogenated castor oil, hydrogenated soybean phospholipid, shellac, sodium alginate, chitosan, fibrin and fibrinogen, agar, carrageenan, guar gum, methyl cellulose (MC), ethyl cellulose, hydroxyethyl cellulose, hydroxypropyl cellulose (HPC), hydroxypropyl methyl cellulose (HPMC), cellulose acetate, hydroxypropyl methylcellulose phthalate, cellulose acetate phthalate, Eudragit®, Carbopol™, polyvinyl alcohol, ethylene-vinylacetate copolymer, ethylene-vinylalcohol copolymer, Crospovidone™, or Pluronic®. Particular examples of extended release agents include HPMC, especially HPMC K100™ and HPMC K15M™, and Eudragit® RSPO.

The formulation may include a solubilising or dissolution agent, and these may be selected from, for example cyclodextrin and its derivate, (e.g. hydroxypropyl-beta-cyclodextrin, methyl-beta-cyclodextrin), polyvinylpyrrolidone (PVP), glucose, mannitol, xylitol, sorbitol, galactose, sucrose, citric acid, succinic acid, polyethylene oxide, polyethylene glycol, sodium starch glycolate, poloxamer, sodium lauryl sulphate, sodium cholate, saponins, silica, oil, triglycerides, surfactants such as Cremophor™, Tween™, solutol HS™, Myrj™, phospholipid and Span™, and alkali materials such as inorganic alkali (e.g. sodium hydroxide and sodium phosphate) and organic alkali (e.g. sodium benzoate and sodium pantothenate). Examples of a solubilising agent include sodium lauryl sulphate, mannitol and sodium starch glycolate.

Tablet formulations may include a lubricant. Lubricants may be selected from, for example, magnesium stearate, stearic acid, calcium stearate, zinc stearate, polyethylene glycol, talc, sodium lauryl sulphate, magnesium lauryl sulphate, adipic acid, and paraffin. Examples of lubricants include magnesium stearate, talc or colloidal silica.

The extended-release formulations of the present invention may be made by any suitable method known in the art, including those described in the latest edition of Controlled Drug Delivery (Drugs and the pharmaceutical sciences; vol. 29; Marcel Dekker, Inc) and the latest edition of Modified-Release Drug Delivery Technology (Drugs and the Pharmaceutical Sciences; vol. 126; Marcel Dekker, Inc).

The extended release oral formulations can be in any suitable form, for example, tablets, capsules, pellets, granules, films and suspensions. An example of an extended release oral formulation is a tablet.

The tablet formulations can be prepared by any suitable tableting method, although direct compression when possible is particularly advantageous and economical as it involves fewer processing steps than other processes. It is also possible to prepare granules and pellets using any suitable technique, including wet granulation, dry granulation and roller compaction. Tablets, capsules, pellets and granules can also be coated using a suitable extended release agent. In exemplary embodiments, wet granulation or direct compression is used. Suitably, a wet granulation technique is used.

Extended-release of the 6-TG in the compositions of the present invention may be achieved with a formulation that includes disaggregating agents, which on contact with biological fluids encourage disaggregation of the formulation.

The 6-TG may also be blended with one or more polymers, to provide a matrix that is either formed into a particle (small or large), or is coated on an inert particle. The polymers are selected from hydrophilic, hydrophobic or plastic polymers. Hydrophilic polymers are water soluble and hydrate in contact with water to form a hydrogel as they dissolve and swell; hydrophobic polymers do not dissolve but may be subject to erosion as the matrix releases soluble constituents; plastic polymers form insoluble or skeletal matrices but do not erode. Upon exposure to the fluid in the stomach, small intestine and colon, hydrophilic polymers hydrate and form a hydrogel that acts as a barrier to drug release; hydrophobic polymers release drug through diffusion through pores and through erosion. Drug release from plastic matrices is controlled by the rate of liquid penetration and is accelerated by the presence of channel forming agents: soluble components that are added in addition to 6-TG.

The rate of 6-TG release can be decreased by increasing the ratio of polymer to 6-TG, and by increasing the hydrophobicity of the matrix. Suitably, the rate of 6-TG release is decreased so as to achieve release in the distal intestine, preferably the colon, after oral administration.

The behaviour of some polymers is pH-dependent, and this property may be used to achieve the desired release profile. A polymer will be especially pH-dependent where it contains acidic or basic moieties and these affect the ionisation state. Ionisation can transform a polymer from being hydrophobic to hydrophilic, with an accompanying transformation in release properties.

The release of 6-TG into, for example, the gastrointestinal (GI) tract may be controlled by the addition of a coating. The coating is typically a polymer or blend of polymers that is relatively stable towards the conditions encountered in, for example, the GI tract. In many cases, the coating includes at least one hydrophilic polymer that will swell on contact with fluid in the gut to form a hydrogel barrier that is homogenous and stable to changes that may take place to the underlying matrix. The hydrogel also serves to slow release of dissolved 6-TG. The properties of the surface coating can be pH-dependent depending upon the presence of acidic or basic moieties in the polymer constituents.

A particular feature of extended release formulations to avoid is the potential for a burst release of drug to occur immediately following contact of the dosage form with the dissolution fluid. The use of a hydrophilic polymer in the film coating or in the matrix, wherein the hydrophilic polymer forms a hydrogel rapidly after hydration, can significantly reduce the incidence of the burst release phenomenon.

Extended release formulations include a monolithic tablet dosage forms in which one or more drug-polymer matrices provide the core, and an optional surface film coating can provide additional control over drug release. This differs from immediate release (IR) formulations which are designed to disintegrate, dissolve promptly and release a bolus dose of drug.

In particular, a matrix may comprise either or both hydrophilic polymers and hydrophobic polymers in order to achieve the appropriate release profile. Further, one or more of the polymers may swell upon hydration in a manner that may additionally be dependent upon pH, to form a hydrogel that is viscous and gelatinous and thus provides a barrier to drug release. The composition of hydrogel determines its properties, which can thus be manipulated in order to achieve appropriate drug release kinetics.

The film coating provides a diffusion release mechanism where the permeability is often directly related to hydration leading to polymer swelling and the installation of hydrogel dynamics.

Multi-layer tablets can be used to provide extended release profiles, or substantially zero order release kinetics. Different layers may also have different release profiles.

At least one combination of matrix and film coating provided in the description below can used to achieve the desired release profile across the different environments encountered during transit through the GI tract. Suitably, the formulation provides a release profile in the distal intestine, preferably the colon. More suitably, the formulation provides a release profile in the colon. In some embodiments, the release rate is approximately 0.2 mg/hour up to 1 mg/hour in the distal intestine.

Microparticulate systems typically consist of spherical particles with diameter 0.05-2.00 mm that are further packaged into a capsule or tablet. Microparticle dosage systems can provide the following benefits for extended release formulations: (1) less dependent on gastric emptying, resulting in less intra/inter individual variability in gastric transit time (sizes less than 2 mm are able to continuously leave stomach even when the pylorus is closed); (2) particles are better distributed, avoiding possibility of localized irritation; and (3) drug safety is improved for extended release formulations, as less susceptible to performance failure if damaged. Furthermore it is possible to mix particles with different release profiles to optimise exposure in different regions of gut.

Polymers that are of use in the formation of drug-polymer matrices are as follows:
(1) acrylic and methacrylic polymers including hydroxypropyl methacrylates (HPMA) and hydroxyethyl methacrylates (HEMA), as well as N-isopropyl acrylamides;
(2) polyethylene oxides (PEO) also known as polyethylene glycols (PEG) and polypropylene oxides (PPO), as well as block copolymers of PEO and PPO (also known as Pluronics®);
(3) cellulose ethers including hydroxypropyl methylcellulose (HPMC), hydroxypropylcellulose (HPC), hydroxyethyl cellulose (HEC);
(4) polylactides (PLA), polyglycolides (PGA), copolymers of polylactide and polyglycolide in various proportions (PLGA);
(5) poly(sucrose acrylates);
(6) polylysine, polyvinylamine, polyethylimine (PEI), polyglutamic acid, polyvinyl alcohol (PVA); copolymers of ethylene and vinyl acetate (pEVA);
(7) polyethyleglycol terephthalate, polybutylene terephthalate and copolymers thereof (e.g., Locteron®); Copolymers of PEG and PLGA (e.g., Re-Gel®); Polyorthoesters (e.g., Chronomer®); polyanhydrides; copolymers of acrylic acids and esters, or methacrylic acids and esters of various molecular weight and proportion (e.g., Eudragit®, in particular RL30D, RLPO, RL100, RS30D, RSPO, RS100, NE30D, NM30D, NE40D, and L100); copolymers of phthalic acid cellulose and phthalic ester cellulose also known as CAP®;
(8) polyvinylpyrrolidone (e.g., Kollidon®) and copolymers thereof with polyvinyl acetate (e.g., Kollidon SR®);
(9) polymers of natural origin including non ionic, amino, carboxylated and sulfated polysaccharides, optionally chemically modified through partial hydrolysis and/or conjugation of modifiers such as carboxylates or long chain fatty acids ($C_8$-$C_{16}$), include guar gum; acacia gum, tragacanth gum, carrageenans (both iota and lambda), Linn gum, alginates, scleroglucans, dextrans, chitins and chitosans, pectins, and galactomannans including locust bean gum.

In addition, it is frequently found that polymer blends are particularly useful for providing the appropriate release profiles for extended release formulations, for example mixing polymers with hydrophilic and hydrophobic properties, and such polymer blends would include:
(1) methyl methacrylates polymers with starch or cellulose polymers;
(2) polyacrylic acid-Pluronic-polyacrylic acid block copolymers;
(3) multilayer polyelectrolytes using cationic polymers selected from chitosan, polylysine, polyallylamine or polyvinylamine with anionic polymers selected from Carbopols® including 971NF, carrageenan, xanthan gum, alginate, hyaluronic acids, and Eudragit® including L100;
(4) hydrophobic cellulose polymers such as ethylcellulose are often mixed with hydrophilic polymers such as HPMC, NaCMC, sodium alginate, xanthan gum or Methocel®;
(5) hydrophilic swelling polymer such as HPMC is mixed with a pH dependant polymer such as Eudragit® L100-55;
(6) polymer blends may be crosslinked either by covalent bonds or, particularly for polymers of natural origin, through the addition of polyvalent cations including borate, calcium, magnesium, zinc;
(7) natural gums are often used in polymer blends, in particular carrageenan with cellulose ethers, xanthan gum with locust bean gum.

In some embodiments, the extended release oral formulation is a tablet. An exemplary tablet comprises 6-TG and one or more polymer binders forming a drug-polymer matrix. In some embodiments the invention provides a pharmaceutical composition comprising 6-TG wherein the composition is a tablet, and comprises, in admixture with 6-TG, a pharmaceutically acceptable carrier selected to provide for the extended release of 6-TG. In some embodiments the pharmaceutically acceptable carrier is a polymer binder, for example hydroxypropylmethyl cellulose.

In some embodiments, polymers used in the formation of 6-TG-polymer matrices include hydroxypropylmethylcellulose; or copolymers of acrylic acids and esters, or methacrylic acids and esters of various molecular weight and proportion (e.g., Eudragit®, in particular RSPO).

In some embodiments, the tablet comprises 6-TG; hydroxypropylmethylcellulose and at least one further pharmaceutically acceptable carrier or excipient. Said further pharmaceutically acceptable carrier or excipient may be selected to modify the release rate of 6-TG, and may include binders such as, but not limited to, disaccharides such as lactose; polysaccharides such as starches and cellulose derivatives, for example, corn starch, starch paste; and sugar alcohols such as mannitol.

In some embodiments the tablet comprises about 1 mg, 5 mg, 10 mg, 20 mg, 25 mg, 30 mg, 40 mg or 50 mg of 6-TG.

In some embodiments, the tablet comprises about 20 mg of 6-TG. In some embodiments, a tablet weighs about 100 mg or 200 mg.

Hydroxypropylmethyl cellulose (HPMC), is commercially available in different viscosities. Exemplary viscosities of hydroxypropylmethyl cellulose are about 100,000 cps; 80,000 to 120,000 cps; and about 15 cps. A suitable HPMC having a viscosity of about 100,000 cps is HPMC K100M. A suitable HPMC having a viscosity of about 15 cps is HMPC K15M.

In some embodiments, the HPMC is HPMC (viscosity 80,000 to 120,000 cps), especially HPMC K100M.

In some embodiments, the HPMC (viscosity about 15 cps) is HPMC K15M.

In some embodiments, the ratio of compound of 6-TG to HPMC in the tablet is 1:1 to 8:1, for example about 1:1 to 4:1; about 2:1 to 4:1; about 2:1 to 8:1 or about 4:1 to about 8:1. In some embodiments the ratio of 6-TG to HPMC (viscosity about 15 cps) is about 1:3.

In some embodiments 6-TG is present in an amount of 10 to 30% w/w of the tablet, especially 15 to 25% w/w of the core, more especially about 20% w/w of the tablet.

In some embodiments 6-TG is present in an amount of 5 to 15% w/w of the tablet, especially about 10% w/w of the tablet.

In some embodiments the HPMC is present in an amount of 2.5 to 30% w/w of the tablet, for example 2.5 to 20% of the tablet; 5 to 20% w/w of the tablet; 10 to 20% w/w of the tablet; or 5 to 10% w/w of the tablet. In some embodiments the HPMC has a viscosity of 80,000 to 120,000 cps. In some embodiments the HPMC (viscosity 80,000 to 120,000 cps) is present in an amount of 2.5 to 20% w/w of the tablet.

In some embodiments, the HPMC (viscosity about 15 cps) is present in an amount of 10 to 40% w/w of the core, for example approximately 30% w/w of the core.

In some embodiments the tablet also comprises one or more pharmaceutically acceptable excipients such as binders and/or lubricants. Suitable binders include disaccharides such as lactose; polysaccharides such as starches and cellulose derivatives, for example, corn starch, starch paste; and sugar alcohols such as mannitol.

In some embodiments, the binder is present in an amount of 40 to 80% w/w of the tablet, especially about 45 to 78% w/w of the tablet.

Suitable lubricants include fats, such as magnesium stearate; talc; or silica, for example, fumed silica.

In some embodiments, the lubricant is present in an amount of 1 to 5% w/w of the tablet, especially about 1 to 4% w/w of the tablet, especially about 1 to 2.5% w/w of the tablet.

In some embodiments, the tablet also includes dissolution or disintegration excipients. In some embodiments a dissolution or disintegration excipient is, for example, sodium starch glycolate or sodium lauryl sulphate.

In some embodiments, the tablet is the formulation according to Formulation 1 (T008), Formulation 2 (T012), Formulation 3 (T025) or Formulation 4 (T038). In some embodiments, the tablet is a tablet of Formulation 9 (T052). In some embodiments, the tablet is a tablet of Formulation 12 (EC-TG052).

Enteric Coating

Optionally, any of the tablet formulations may include an enteric coating. An enteric coating controls the release or 6-TG by preventing release in the stomach and by reducing or substantially preventing release of 6-TG prior to the tablet reaching the distal intestine. Suitable enteric coatings include cellulose coatings such as cellulose acetate phthalate polymers or hydroxypropyl methylcellulose phthalate polymers or co-polymers of acrylic acids and their esters or methacrylic acids or their esters, such as those sold under the trade mark Eudragit® including L100, L100-55 and S100. In one embodiment the coating is Eudragit® S100.

The enteric coatings may also comprise lubricants. The enteric coatings may also comprise plasticisers. The enteric coatings may also comprise anti-tacking agents.

Enteric coatings may be applied to a tablet using conventional techniques known in the art. For example, a coating may be applied using dip coating or pan coating technology as described in, for example, *Remington: The Science and Practice of Pharmacy*, Loyd V. Allen, Jr (Ed), The Pharmaceutical Press, London, $22^{nd}$ Edition, September 2012 at Chapter 46.

Extended-release formulations within the scope of the present invention can be prepared in accordance with the description provided herein.

Dosage Levels

In specific embodiments, the optimal therapeutic protocol, and thus the methods of the present invention comprise administration of a total daily dose of 6-TG of about 0.1 mg/kg, 0.2 mg/kg or 0.3 mg/kg body weight to about 2.5 mg/kg body weight, for example 0.1 mg/kg body weight to 2.5 mg/kg body weight. Suitably the total daily dose of 6-TG is 0.1, 0.2 or 0.3 mg/kg body weight to 2.0 mg/kg body weight; 0.1, 0.2 or 0.3 mg/kg body weight to 1.5 mg/kg body weight; or 0.1, 0.2 or 0.3 mg/kg body weight to 1 mg/kg body weight. More suitably the total daily dose of 6-TG is from 0.3, 0.4 or 0.5 mg/kg body weight to 1.0 mg/kg body weight, and even more suitably the total daily dose of 6-TG is about 0.3, 0.4 or 0.5 mg/kg body weight to about 0.8 mg/kg body weight. Suitably, the dose is administered as a once daily dose.

It will be appreciated by those skilled in the art that the dosages above, although recited as a daily dosage, may not be administered on a daily basis. For example, a daily dose of 6-TG of 0.1 mg/kg/bodyweight to 1 mg/kg/body weight may be administered every 2, 3, 4, 5, 6, or 7 days (or otherwise). In an illustrative embodiment, and individual (e.g., adult) of 60 kilograms receiving a daily dose of 6-TG of 1 mg/kg/body weight (i.e., a daily dose of 60 mg) may receive 60 mg/day or may instead receive 120 mg every 2 days, or 180 mg every 3 days, etc. In another illustrative embodiment, an individual (e.g. child) of 20 kilograms may receive the same daily dose of 6-TG (1 mg/kg/body weight) equating to 20 mg/day, or 40 mg/2 days or 60 mg/3 days, etc.

Accordingly, in certain embodiments the composition of the present invention comprising 6-TG comprises between 0.3 mg/kg body weight and 2.5 mg/kg body weight of 6-TG. Suitably the composition comprises between 0.4 mg/kg body weight and 1 mg/kg body weight of 6-TG, more suitably the composition comprises between 0.5 mg/kg body weight and 1.0 mg/kg body weight of 6-TG, and even more suitably the composition comprises between 0.5 mg/kg body weight and 0.8 mg/kg body weight of 6-TG.

The precise dosage of 6-TG in the compositions of the present invention can depend on a variety of factors, such as the intended mode of administration, the disease or condition to be treated, the progression or stage of the disease or condition, and/or the individual to be treated, including the age, gender, height, and/or weight of the individual. It is expected that the precise dosage can be determined by a practitioner in the art. In determining the dosage, the practitioner may evaluate the severity of the disease or condition, or the severity of the symptoms of the disease or condition, the individual's clinical history and responsiveness to previous therapies including any history of prior relapse of the disease or condition. It is expected that the dosage may be readily determined without undue experimentation.

EXAMPLES

Animal Experiments and Treatments

All the animal experiments were approved by the University of Queensland Animal Ethics Committee. C57Bl/6 wild-type (WT) mice were purchased from the Animal Resource Authority, Western Australia and the Hprt$^{-/-}$, Winnie and RaW were bred in-house in a pathogen free animal facility. Male or female mice were intra-gastrically gavaged daily with either vehicle control or thiopurine drugs (6-TG or 6-MP) for periods between 14 and 28 days. 6-TG or 6-MP were also administered intra-rectally to Winnie mice. 6-TG (MW 167, ex Sigma-Aldrich) was prepared as a suspension in water and mixed thoroughly before administration. 6-MP (MW 170, 6-MP monohydrate, ex Sigma-Aldrich) was dissolved in water. The vehicle control was water.

Dextran sodium sulphate (DSS) (36-50 kDa; MP Biochemicals) was administered in the drinking water chronically [0.5% (w/v) for 4 cycles of 5 days on, followed by either 7 or 9 days off].

Histological Colitis Scoring

Histological assessment of spontaneous and DSS induced colitis was performed blinded to mouse genotype and treatment as described in C. K. Heazlewood et al., PLoS medicine 5, e54 (2008). For Winnie and RaW mice this was based on the extent of the inflammatory infiltration, number of neutrophils, goblet cell loss, crypt architecture, abscess and length, tissue damage; for DSS induced colitis the histological score was based on the degree and extent of tissue damage and inflammation.

Diarrhoea Scores

Diarrhoea scoring for both spontaneous and DSS induced colitis was performed daily by unblinded multiple scorers for the duration of the experiments. The diarrhoea score was coupled with a rectal bleeding score in the Winnie and WT DSS experiments (Combined Diarrhoea Score). The diarrhoea score ranged from 0 to 3, 0 being no and 3 being frank diarrhoea; rectal bleeding ranged from 0 to 3, 0 no bleeding and 3 frank rectal bleeding. For DSS induced colitis in Hprt$^{-/-}$ mice the composite disease activity index (DAI) score was used and this comprised diarrhoea, rectal bleeding and body weight percent loss subscores (0<1% loss; 1=1-5% loss; 2=5-15% loss; 3>15% loss).

FACS Analysis

At culling point immune organs were collected and transferred in ice cold media and they were harvested and teased apart into single cell suspension by pressing with plunger of a syringe into a 40 µM sterile cell strainer (BD Falcon). Cells were pre-incubated with 1:200 of anti-CD16/CD32 (Fc block from eBioscience) for 5-10 mins on ice prior to staining. After washing and removing supernatant containing Fc block, cells were resuspended in cocktail mix which comprised the following antibodies: CD11c, MHCII, CD11b, CD3e, CD4, CD69, CD8 and CD19 (BD-Pharmingen, Australia). 7AAD was used in order to exclude debris and necrotic cells and was read in the PerCP-Cy5-5 channel. Flow cytometry analysis was performed on LSRII (BD Biosciences), and data was analyzed using FlowJo software.

6-TGN Measurement

For in vitro experiments with bacteria (*Escherichia coli* PC1101, *Enterococcus* faecalii ATCC 19433 and *Bacteroides thetaiotaomicron* AMC0002), 6-TGN in 3× washed bacterial pellet was measured as 6-TG riboside (6-TGr) by converting the intracellular 6-TGN to TGr. This was achieved by acid phosphatase (Sigma) incubation of cellular sonicates for 30 minutes at 37° C. TGr was measured by HPLC-UV using an Altima HP C18 column. In mouse samples, a modified Dervieux method (Dervieux T. eta., *Clinical chemistry*, 2074-2084 (2005) was used for measurement of TGN by LC-MS/MS (Shimadzu LC 20 HPLC system coupled to API 3200 tandem mass spectrometer). After tissue homogenization perchloric acid 35% and DTT 100 mg/mL were added and the samples were centrifuged at 3500 g at 4° C. for 60 s. The supernatant was divided into two aliquots of equal volume; one of these aliquots was boiled at 100° C. for 60 minutes. 6-TGN was quantification was performed by subtracting the quantity of 6-TG in the unboiled sample from that of the boiled sample (in which all 6-TGNs are reduced to 6-TG).

Cell Cultures

HeLa, HCT116, HT29, HepG2 and RAW cells were obtained from ATCC and grown in DMEM supplemented with GlutaMAX (Life Technologies), 10% fetal calf serum and 20 µg/ml penicillin/streptomycin. HeLa cells stably expressing LC3-GFP have been described previously (Kabeya Y et al., The EMBO Journal, 2000, 19(2), 5720-5728; Birmingham C L et al, J. Biol. Chem., 2006, 281(16), 111374-11383). Primary fibroblasts isolated from WT and Hprt$^{-/-}$ mice were generated from ear punch samples after dissociation with trypsin and cultured in DMEM supplemented with Glutamax and 20% fetal calf serum with antibiotics and passaged up to four times to ensure that they were axenic.

Bulk Autophagy Assay/Western Blot.

To measure autophagy induction, cell lines were plated at 70% confluence and treated for indicated time with 6-TG 10, 50 and 100 µM with or without the addition of 10 µg/ml of E64D-Pepstatin A (Sigma) or mock treated with DMSO 0.1%. Following treatment cells were treated with TNN (Tris-HCl, NaCl, NP40) lysis buffer. Western blotting to demonstrate LC3 lipidation was performed after equalization of protein amounts and SDS-PAGE electrophoresis on a 4-12% NuPAGE BisTris gel (Invitrogen). Following transfer to PVDF membranes (Invitrogen), detection was performed using rabbit anti-LC3 primary (Sigma), mouse anti-Actin (Sigma) and appropriate fluorescent secondary antibodies (LI-COR Biosciences) and imaged on a LICOR fluorescent imaging system.

Antibacterial Autophagy Assay

*S. Typhimurium* infections of HeLa cells and gentamycin protection assays were performed as described in Poppe, D. et al, *J. Immunol.* 176, 640-651 (2006). Briefly HeLa cells were plated in 12-well plates containing 18 mm glass coverslips at a density of 1×10$^5$ cells per well in DMEM 24 hours before infections. Cells were treated with TG or mock treated with DMSO for 16 hours prior to infection. *S. enterica* serovar *Typhimurium* SL1344 carrying a DsRed2 expression plasmid was grown overnight in Luria-Bertani broth containing 100 µg/mL carbenicillin at 37° C. with aeration and subcultured at a dilution of 1/33 for a further 3 h in Luria-Bertani carbenicillin broth. This culture was further diluted in DMEM 10% serum without antibiotics to yield a multiplicity of infection (MOI) of 100 and added to HeLa LC3-GFP cells. Infections were allowed to proceed for 20 minutes and the cells were washed once in complete medium containing 100 µg/mL gentamicin sulfate and then incubated in fresh high gentamicin medium for an additional 40 minutes. Cells were washed twice in PBS before methanol fixation/permeablization, nuclear counterstaining with Hoechst 33342 (Invitrogen) and mounting with Prolong-Gold (Invitrogen). Slides were viewed for counting under wide-field fluorescence illumination with a 60× lens (Olympus). The fraction of LC3-GFP-positive bacteria per cell was assessed in randomly chosen fields with at least 90 cells counted for each condition. Bacteria were scored as within autophagosomes only when a complete and closely conforming LC3-GFP "capsule" was visible.

Bacterial Replication Assay

Gentamicin protection replication assays in HeLa cells were performed by using bioluminescent *Salmonella typhimurium* containing Xen33 (Perkin-Elmer). HeLa cells were infected as above in 96 well plates and after 40 minutes cells were washed twice with PBS and then media containing 20 µg/mL gentamicin was added to wells. Plates were read at 12 h.

Statistics and Analysis

Mann-Whitney was used for non-parametric data that were graphed as box and whisker plots with median, quartiles and range. For the time and dose related experiments the significance was assessed by two-way ANOVA with Bonferroni post-test corrections. Significance of a result is shown by a * to indicate test versus WT TG 0 mg/kg, and a # to indicate test versus Hprt$^{-/-}$, Winnie and RaW TG 0 mg/kg. Statistics: * or # or & P<0.05,  or ## or &&P<0.01, * or ### or &&&P<0.001.

Example 1

High-Dose 6-TG Improved the Spontaneous Colitis in the Winnie Model of Ulcerative Colitis in 14 Days Winnie mice develop a spontaneous colitis resembling ulcerative colitis, which emerges by four weeks of age. The initiating factor is a defect in goblet cell mucin production due to a single nucleotide polymorphism in the D3 domain of Muc2, which leads to protein misfolding and endoplasmic reticulum (ER) stress in the mucin-secreting cells, resulting in a Th17 predominant colitis.

Figure 2A:
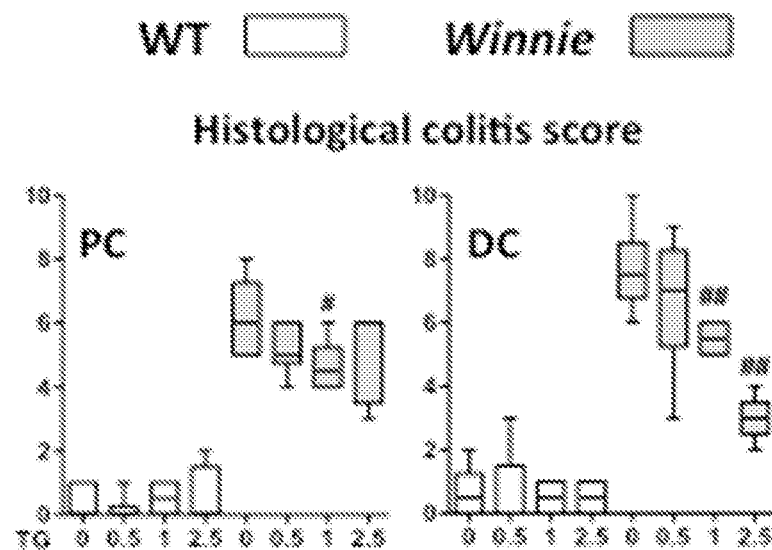
FIGS. 2A-2C shows data demonstrating that acute administration of 6-TG improved spontaneous colitis in Winnie mice. C57Bl/6 (WT, open symbols) or Winnie (grey symbols) mice were daily gavaged 6-TG 0, 0.5, 1 or 2.5 mg/kg for up to 14 days.
Figure 2B:
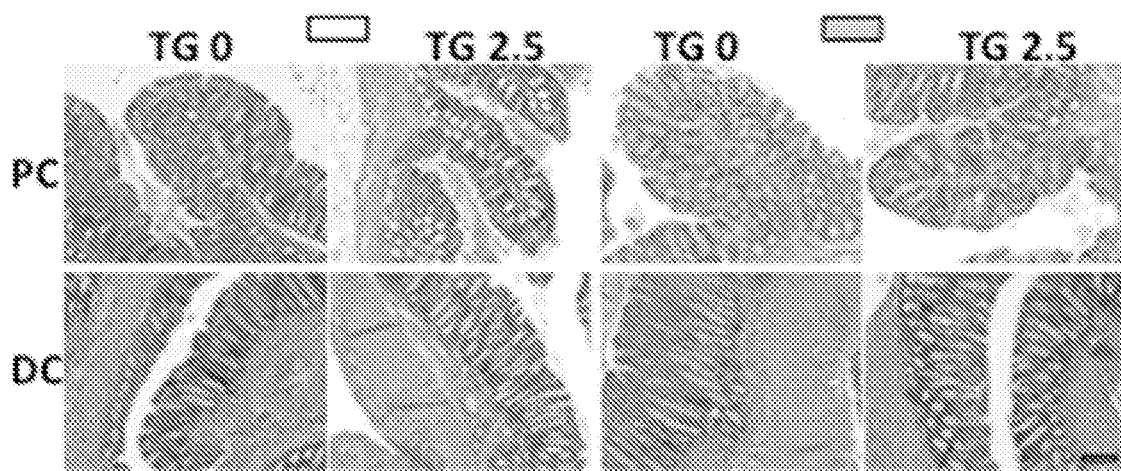

Juvenile Winnie and wild-type C57Bl/6 (WT) control mice were gavaged daily with either vehicle control or 6-TG at concentrations of 0.5, 1 or 2.5 mg/kg for up to 14 days. FIG. 2A shows that 6-TG 1-2.5 mg/kg ameliorated the spontaneous colitis in a dose-dependent manner. Both the colitis and its improvement with treatment [FIG. 2A and 2(B)] were more marked in the distal colon (DC) of the Winnie mice. This demonstrates the speed of onset and efficacy of 6-TG in the Winnie mice model of spontaneous colitis.

Example 2

Figure 3D:
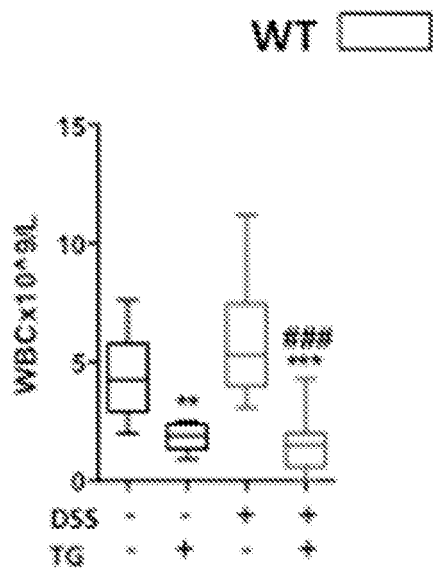

Administration of Clinically Relevant Low Dose of 6-TG (but not 6-MP) Over 28 Days Improved the Spontaneous Colitis in Winnie, and Also Chronic DSS-Induced Colitis in WT Mice Winnie mice were daily gavaged with 6-TG (0.5 mg/kg/d) or 6-MP (2.5 mg/kg/d) for 28 days. 6-TG, but not 6-MP, tended to reduce peripheral blood leukocytes [P=0.09, FIG. 3A]. Winnie mice improved with 6-TG but not with 6-MP over the 28 days with respect to the combined diarrhoea (combined diarrhoea and rectal bleeding) score [FIG. 3B] but the colon weight/length ratio was unchanged. 6-TG improved blinded histological colitis scores in both PC and DC [FIG. 3C].

Figure 3E:
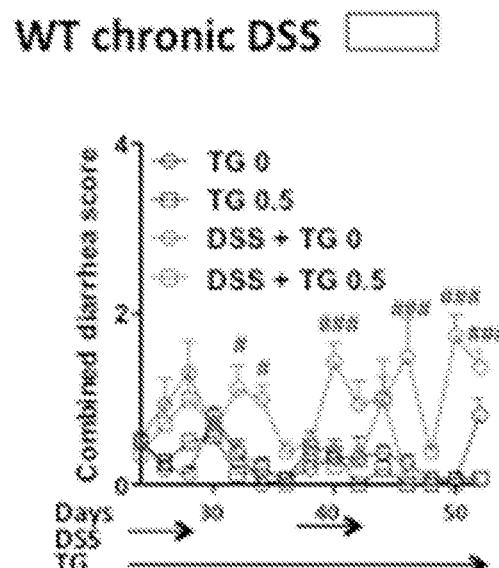
Figure 3F:
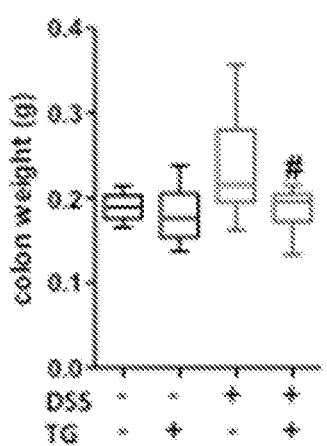

Low dose 6-TG also ameliorated a chronic colitis, which was induced in C57Bl/6 WT by 0.5% DSS administration in drinking water for 4 cycles. These mice were daily gavaged 6-TG 0.5 mg/kg from day 25 for a total of 28 days (last 2 on-off DSS cycles). The 6-TG treatment was associated with decreased peripheral white blood cells in both DSS-treated and untreated WT mice [FIG. 3D]. The combined diarrhoea score [FIG. 3E] and colon weight [FIG. 3F] were significantly improved with 6-TG. The DSS colitis was also improved with 6-TG as evidenced by total colitis scores [FIG. 3G], and immune and epithelial damage subscores.

Figure 3G:
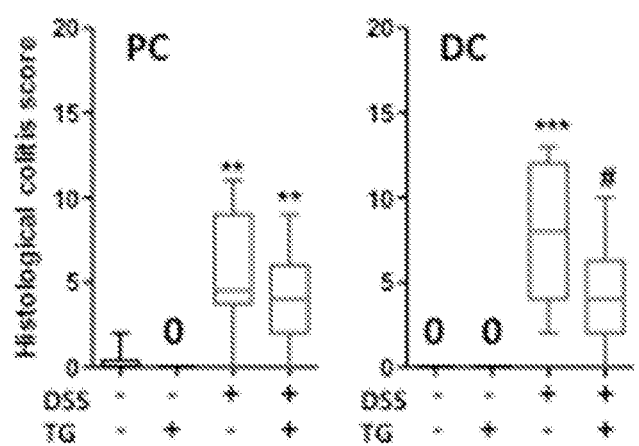

While the combined diarrhoea score improved with treatment [FIG. 3G], the disease activity index (DAI)—a composite of % body weight loss, diarrhoea and rectal bleeding scores—was not significantly altered because 6-TG treatment, irrespective of DSS, was associated with a reduction of expected body weight gain in the juvenile C57Bl/6 WT mice. Colon weight/length ratio was also not improved.

The results demonstrate that 6-TG acts faster than 6-MP in the murine models, with respect to the speed of onset and efficacy in ameliorating colitis induced by DSS in WT mice.

Example 3

6-TG has a Therapeutic Effect Independent of T Lymphocytes

T and B lymphocytes are not required for the occurrence of spontaneous colitis in Winnie mice. Winnie×Rag$^{-/-}$ (RaW) mice are Winnie mice that lack T and B lymphocytes. RaW mice spontaneously develop a colitis phenotype with more proximal disease than Winnie [Eri, R D et al; *Mucosal. Immunol.* 4, 354-364 (2011)].

Figure 4A:
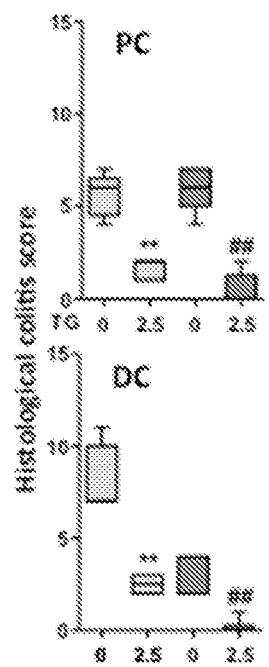
FIGS. 4A-4B shows data confirming that 6-TG has a therapeutic effect independent of T lymphocytes. $Rag^{-/-}$ mice lack T and B lymphocytes. They were crossed with Winnie mice to yield a RaW mouse without T and B lymphocytes that has a spontaneous colitis.
Figure 4B:
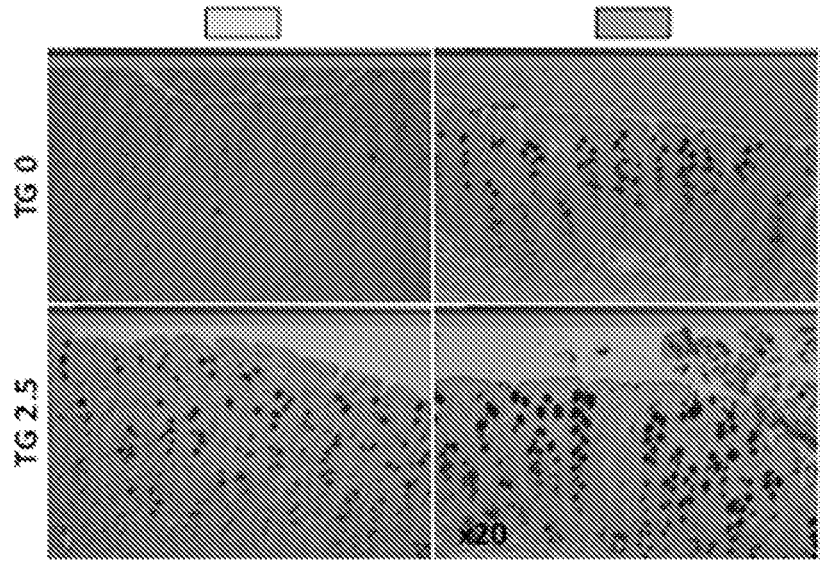

In an experiment with Winnie and RaW mice strains, 6-TG 2.5 mg/kg administration for up to 14 days improved colon weight/length ratio, improved blinded histological PC and DC colitis scores [FIG. 4A], and restored goblet cell morphology in both RaW and Winnie mice [FIG. 4B]. 6-TG treatment was also associated with decreased inflammation (improved Ifn-γ, Il-1b) and increased Muc2 expression in both the PC and DC of RaW mice and the Winnie controls.

These data suggest that 6-TG may ameliorate colitis not only through adaptive T lymphocyte mediated immune responses, but also through innate immunity because lymphocytes are not essential either for colitis, or 6-TG treatment.

Example 4

Low Dose 6-TG Improved Chronic DSS Induced Colitis in HPRT$^{-/-}$ Mice

Hprt$^{-/-}$ mice were permitted 0.5% DSS (to induce gut inflammation) or water ad libitum and 6-TG was administered at 0.5 mg/kg from day 28 to day 52 by oral gavage. Clinical outcomes in terms of gut inflammation were assessed by disease activity index (DAI).

The results are shown in FIGS. 5A-5G and demonstrate that there is a rapid and appreciable reduction in disease activity in Hprt$^{-/-}$ mice in which colitis was induced with DSS.

Figures 5A, 5B:
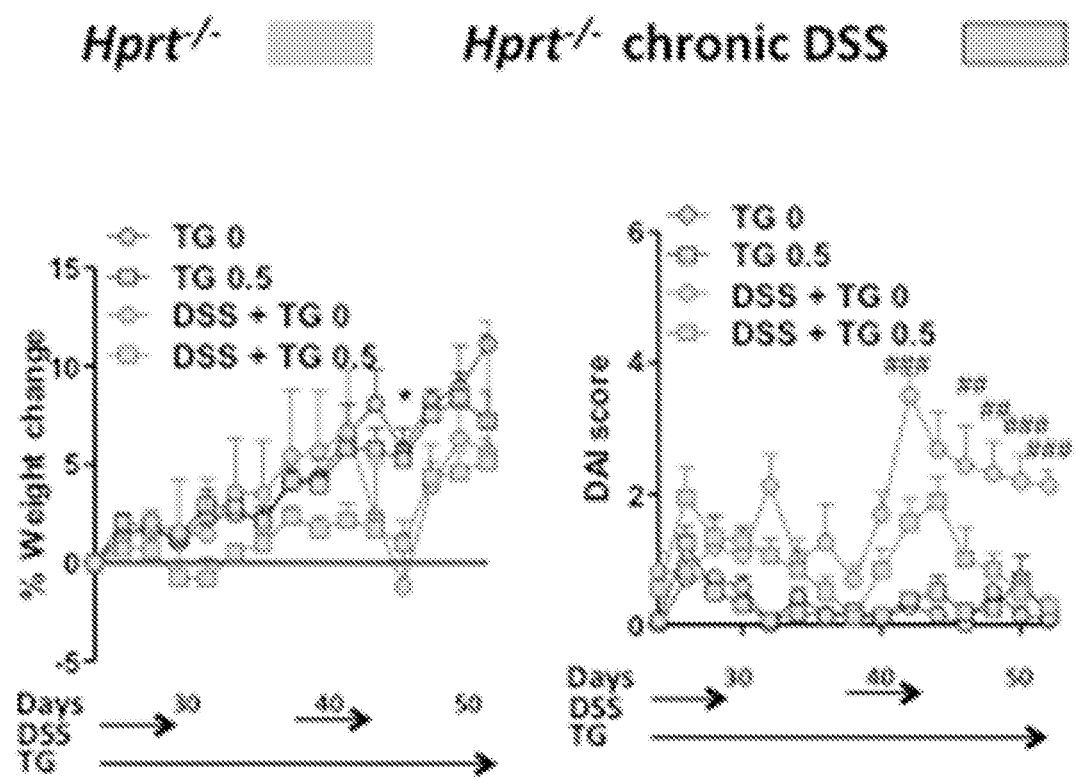
FIGS. 5A-5G shows data confirming that low dose 6-TG improved chronic induced colitis in $Hprt^{-/-}$ mice. $Hprt^{-/-}$ mice were administered either water or 0.5% DSS in drinking water for 4 cycles and daily gavaged with 6-TG 0 or 0.5 mg/kg for the last two cycles (28 days)
Figure 5C:
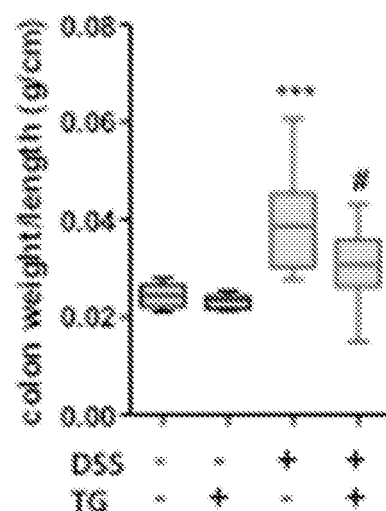
Figure 5D:
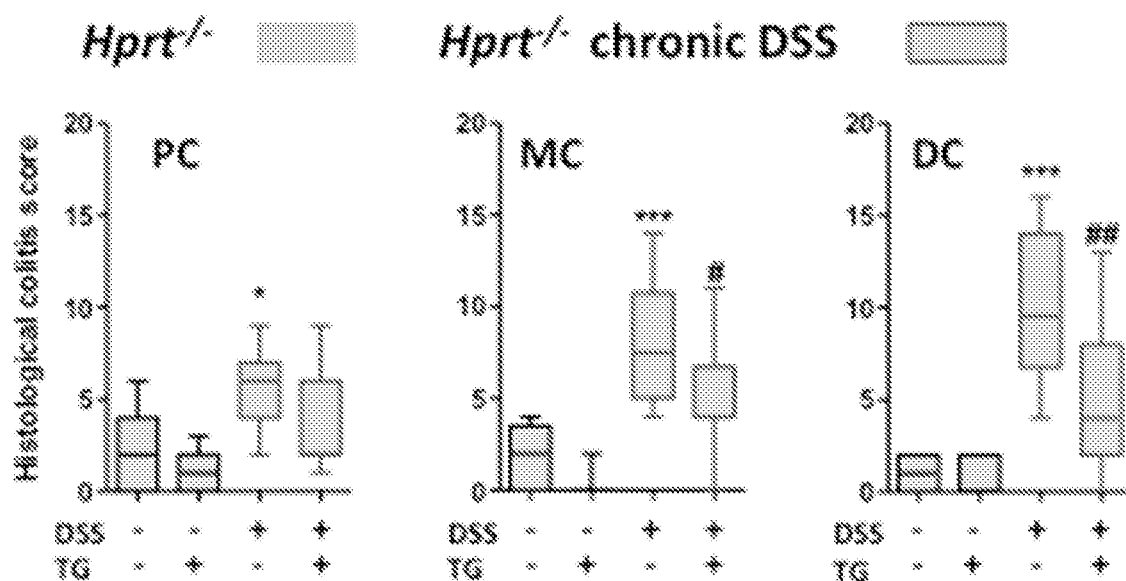
Figure 5E:
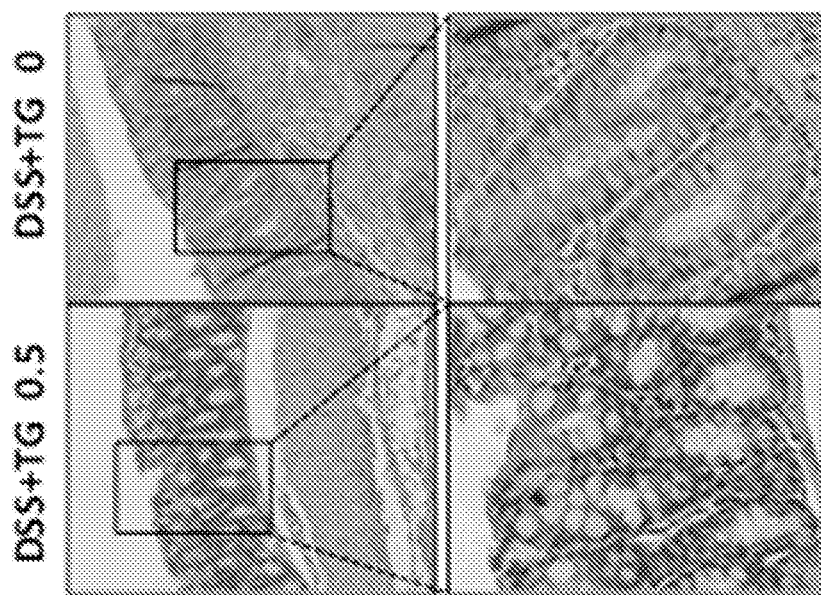
Figure 5F:
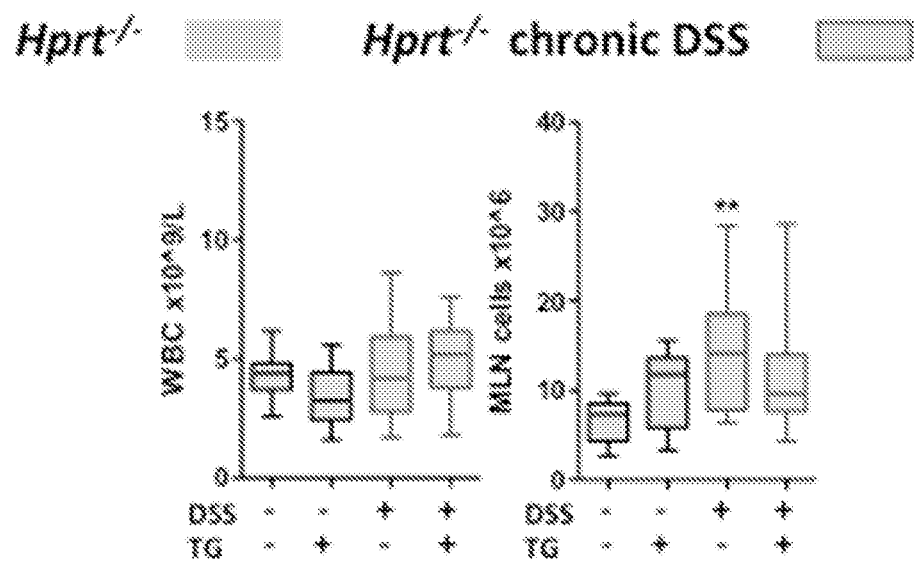
Figure 5G:
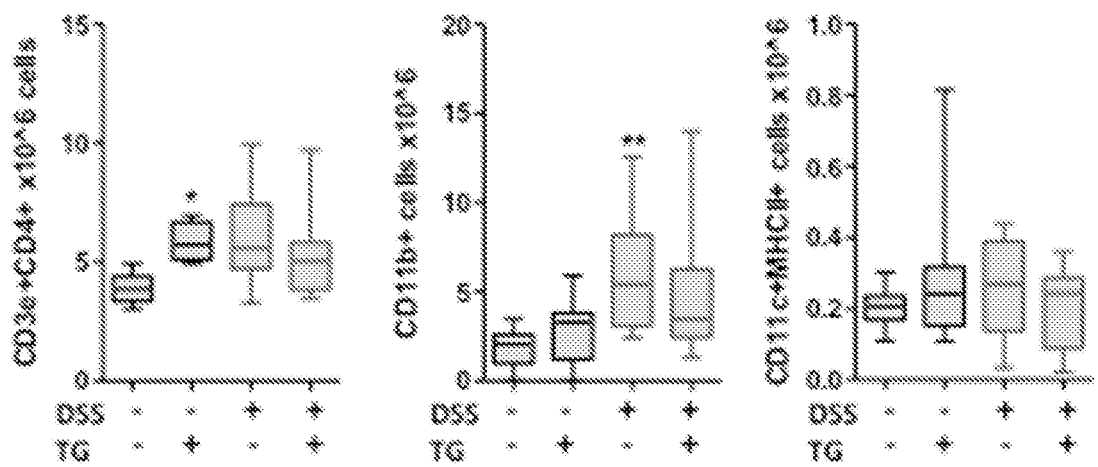

Metabolism of 6-TG to 6-TGTP is required for the action of 6-TG. It was hypothesised that 6-TG would not improve chronic DSS colitis in Hprt$^{-/-}$ mice because of the requirement for hypoxanthine (guanine) phosphoribosyltransferase (HPRT) enzyme for metabolism of 6-TG. Unexpectedly, in the DSS induced colitis in Hprt$^{-/-}$ mice, 6-TG treatment was associated with improvement in all of the outcome measures: body weight scores, the disease activity index (DAI) that includes diarrhoea, body weight change and rectal bleeding scores, colon weight/length ratio [FIG. 5A-5C], colon weight and histological colitis scores of the different colonic segments [FIG. 5D]. Representative H&E histology showed a more normal epithelium with intact goblet cells [FIG. 5E]. The 6-TG treatment was not associated with immunosuppression in Hprt$^{-/-}$ mice since immunosuppression is related to generation of systemic 6-TGTP [FIG. 5E]. In addition, MLN cell counts in the Hprt$^{-/-}$ mice were expectedly increased by DSS in association with colitis but not depressed by 6-TG [FIG. 5F]. FIG. 5G shows that CD3e+CD4+, CD11b+ and CD11c+MHCII+ subset numbers in the MLN were not decreased by 6-TG administration in untreated or DSS exposed Hprt$^{-/-}$ mice.

These data indicate that the therapeutic action of 6-TG in ameliorating a chronic DSS colitis in Hprt$^{-/-}$ mice does not require host 6-TGTP production and is not associated with systemic immunosuppression.

It was further noted that the microbiome is slightly altered by 6-TG to produce a less colitogenic microbiome.

Example 5

Intra-Rectal 6-TG Ameliorated Spontaneous Colitis within 14 Days

Winnie mice were treated daily with intra-rectal 6-TG 1 mg/kg or 6-MP 1 mg/kg. White cell counts were not significantly different after 14 days intra-rectal treatment with mean white cell count (SD) for 6-TG 8.7 (1.4), 6-MP 12.3 (1.5) and control 11.0 (1.5). The 6-TG-treated mice had statistically significant improvement of combined diarrhea score from day 11 [see FIG. 6A] and colon weight/length ratio [FIG. 6B] compared to 6-MP and vehicle control treatments. Blinded histological scoring of the distal colon confirmed a striking improvement with 6-TG but not with 6-MP in the distal colon (see FIG. 6C, P<0.01). There was no improvement in colitis in mid-colon or proximal colon indicating that the beneficial effect on colitis was local [FIG. 6C].

Example 6

Bacteria Convert 6-TG, but Less so 6-MP, to Thioguanine Nucleotides (6-TGN)

Having shown in the Hprt$^{-/-}$ mice that 6-TG improved colitis in the total absence of systemic immunosuppression, it was investigated whether the host's microbial metabolism could be generating 6-TGTP.

Figure 6D:
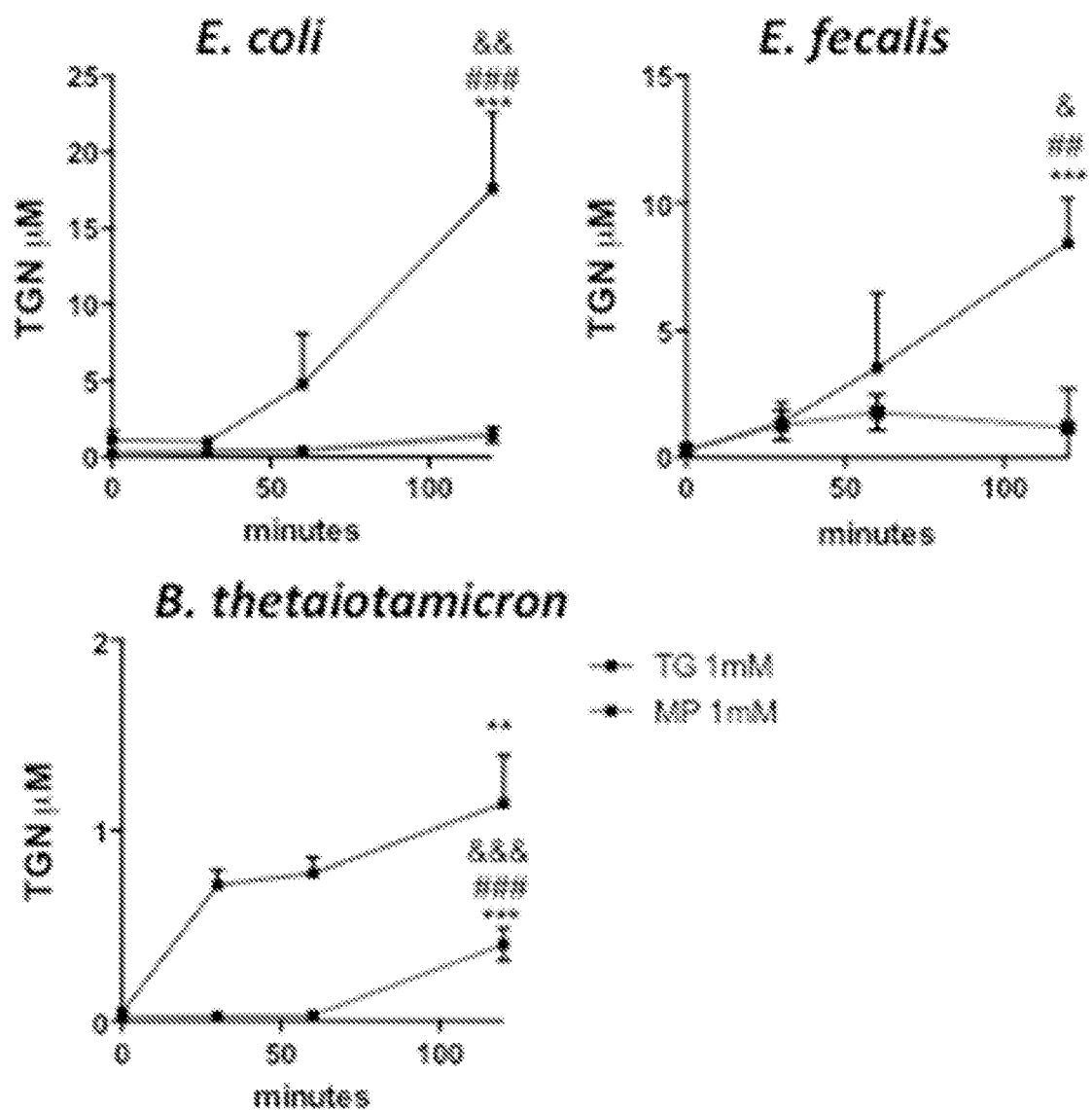

Bacterial metabolism of 6-TG was investigated in vitro using the representative gut bacteria *Escherichia coli*, *Enterococcus faecalis* and *Bacteroides thetaiotamicron*. 6-TGN (6-TGMP, 6-TGDP and 6-TGTP) were found in the bacterial pellets following incubation of log phase cultures of all three bacterial strains with 1 mM 6-TG for 120 minutes [FIG. 6D]. In contrast, generation of 6-TGN was minimal over this time period when cultures were incubated with 1 mM 6-MP. 6-TGN were also detected by LC-MS/MS (FIG. 6E) when faecal slurries derived from Hprt$^{-/-}$ were incubated with 5 or 10 μM 6-TG for 6 h [FIG. 6F]. These data indicate that laboratory and gut bacteria are able to metabolize 6-TG to the active 6-TGN metabolites.

When WT and Hprt$^{-/-}$ mice were gavaged daily with 6-TG 5 mg/kg for 10 days, 6-TGN were found in faeces of both strains and the liver of WT but not in the liver of the Hprt$^{-/-}$ mice [FIG. 6G]. Thus, the therapeutic action of 6-TG in the Hprt$^{-/-}$ mice may arise from bacterial HPRT conversion of 6-TG to 6-TGTP, in which the local production of 6-TGTP by bacteria may be sufficient to ameliorate colitis.

Example 7

6-TG Enhances Autophagy In Vitro in a 6-TGN Dependent Manner

Based on the improvement of colitis with increased epithelial health in DSS Hprt$^{-/-}$ mice treated with 6-TG, the lack of extra-colonic anti-inflammatory effect in the Hprt$^{-/-}$ mice, and the rapid response to intra-rectal 6-TG in Winnie mice, the influence of 6-TG or 6-TGTP on the bacterial-epithelial interaction was investigated. Epithelial cells rely on autophagy to respond to luminal bacteria and maintain homeostasis, and impaired antibacterial autophagy in the gut has been hypothesised to be a contributor to IBD.

Figure 7C:
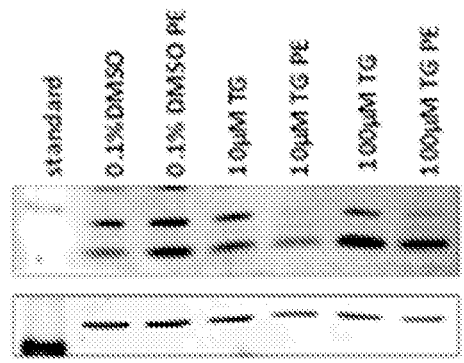
Figure 7C:
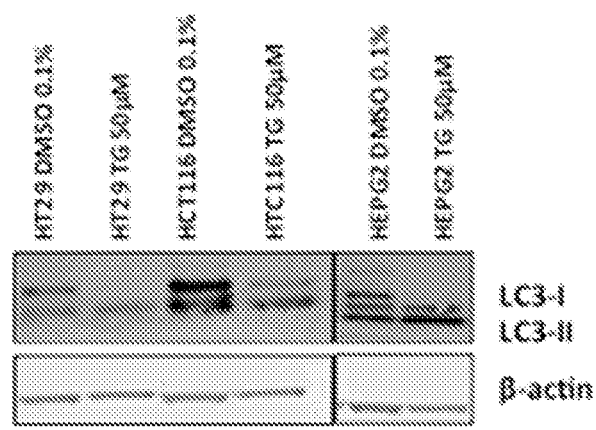
Figure 7C:
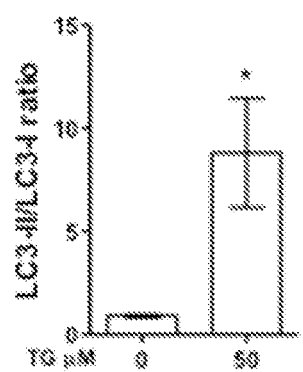
Figure 7D:
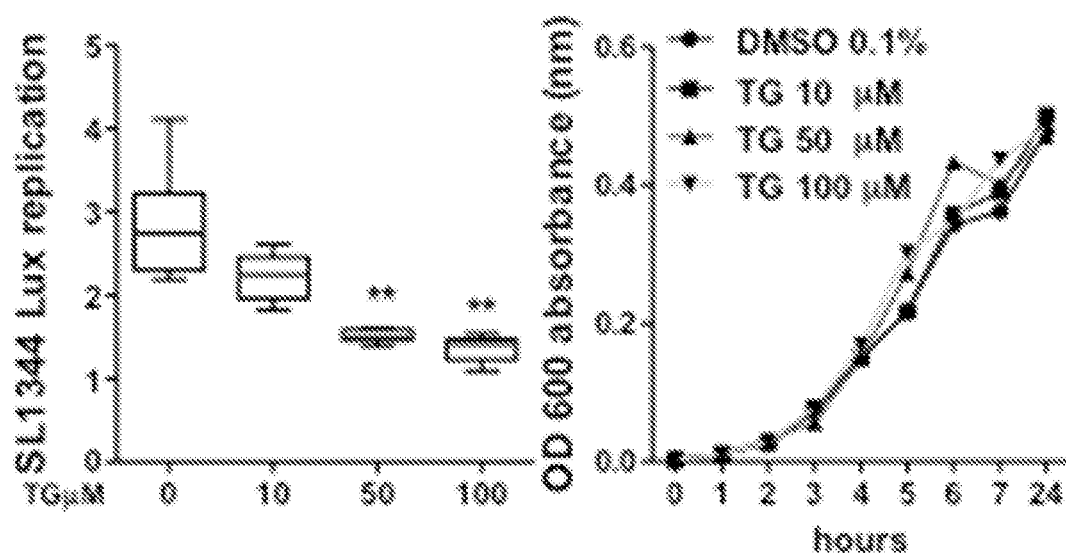
Figure 7E:
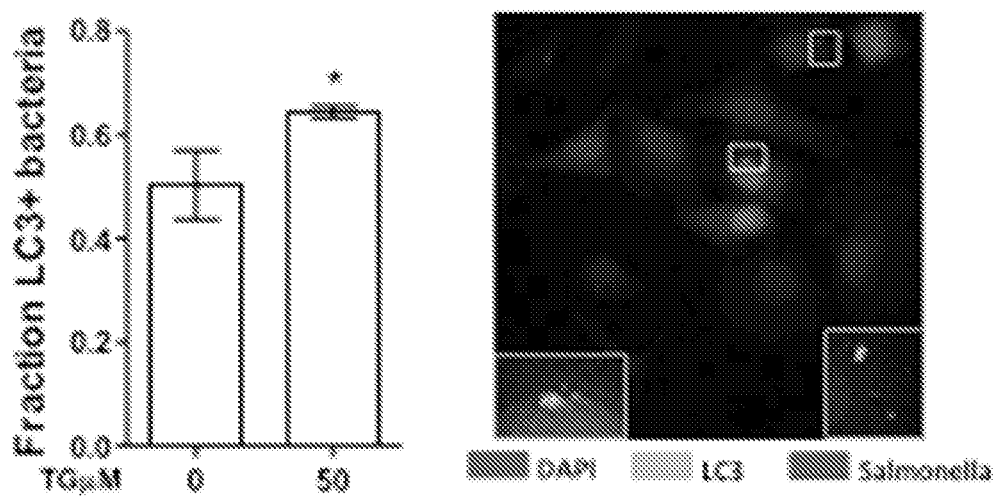

The effect of 6-TG on bulk autophagy was investigated by monitoring the conversion of LC3I to LC3II. HeLa cells were incubated for 16 hours with either vehicle control or 6-TG 10 and 100 μM with or without PepstatinA and E64D (PE) to examine autophagic flux. 6-TG treatment increased the LC3II to LC3I ratio [FIG. 7A], indicative of increased autophagosome accumulation. Treatment with PE, which blocks autophagosome maturation and recycling of LC3II back to LC3I, further augmented the effect indicating that the effect of 6-TG is due to increased autophagic flux rather than inhibition of maturation. This effect was also observed in human gut epithelial cell lines (HT29, HCT116) and hepatocytes (HepG2) [FIG. 7B], and also in murine RAW macrophage-like cells [FIG. 7C]. To determine if 6-TG treatment had an effect on intracellular bacterial handling, a *Salmonella* intracellular replication model, which is known to be sensitive to effects on antibacterial autophagy, was investigated. HeLa cells were pretreated with vehicle control or 6-TG and infected with bioluminescent *Salmonella typhimurium* (SL1344) and replication monitored by measuring luminescence. Treatment with either 50 or 100 μM 6-TG significantly decreased intracellular replication of the bacteria [FIG. 7D]. The autophagosome encapsulation of bacteria was further quantified by fluorescence microscopy with or without treatment with 6-TG 50 μM in HeLa cells expressing LC3-GFP. This dose of 6-TG significantly increased LC3 co-localization with intracellular bacteria compared to control consistent with increased anti-bacterial autophagy [FIG. 7E].

In order to differentiate between 6-TG or 6-TGTP effect, primary fibroblasts isolated from WT and Hprt$^{-/-}$ mice were incubated for 16 hours with either vehicle control or 6-TG 50 μM. There was minimal LC3-I observed in fibroblasts but the LC3-II to β-actin ratio was significantly increased in the 6-TG treated WT derived fibroblasts, consistent with induction of autophagy, but there was no effect in the absence of Hprt [FIG. 7F], although autophagy could be induced in Hprt$^{-/-}$ fibroblasts by the mTor inhibitor, Torin1. Together these data show that 6-TG treatment of epithelial cells induces autophagy in a 6-TGTP dependent manner and improves restriction of intracellular bacterial growth, likely through induction of antibacterial autophagy.

Figure 2C:
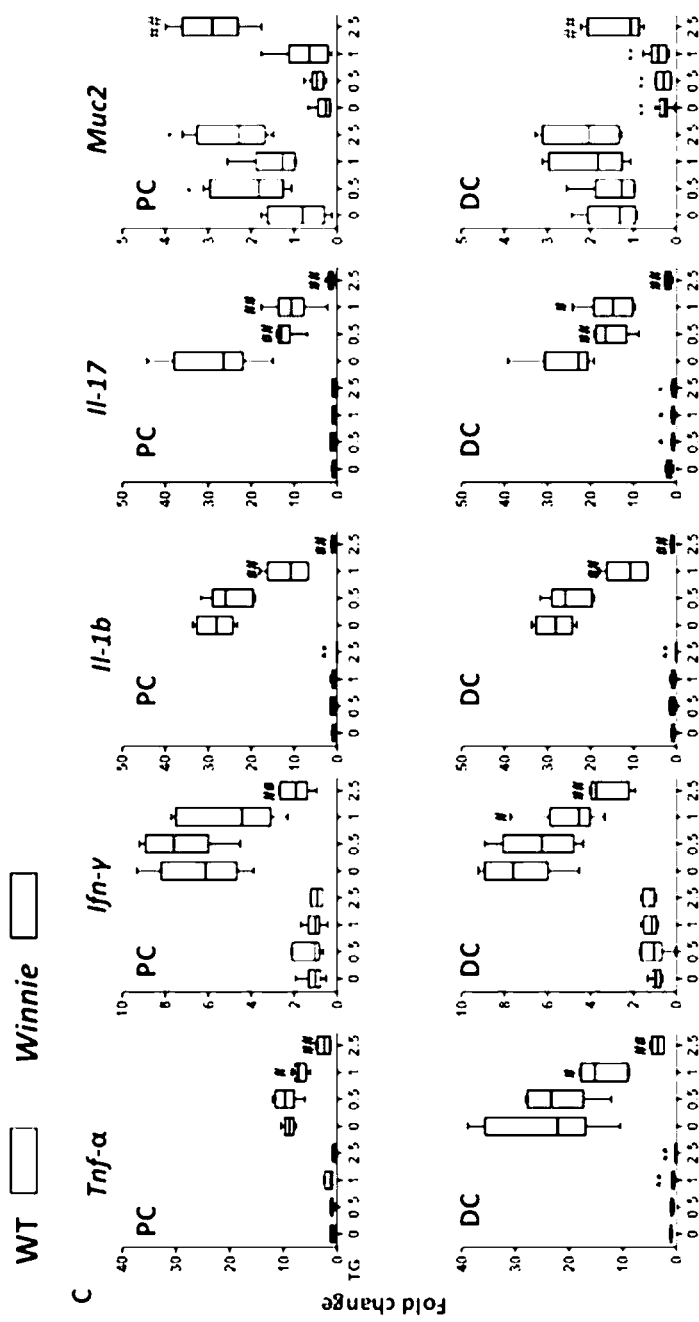

The action of 6-TG to ameliorate colitis was rapid, and the degree of rapidity of action was unexpected. The pharmacodynamic effect of oral and intra-rectal TG treatment in the Winnie mice was less than two weeks as manifest by the improved colonic histology with 6-TG 1 or 2.5 mg/kg/day (FIGS. 2A-2C), the fast symptomatic improvement in the DSS-induced colitis in WT and Hprt mice treated with low dose 6-TG (FIGS. 2A-2C, FIGS. 5A-5B), and the rapid symptomatic and histological improvement in Winnie mice with intra-rectal TG (FIGS. 6A-6G).

The rapidity of the pharmacodynamic effect of 6-TG but not 6-MP in the murine colitis experiments, is not well explained by the pharmacokinetic differences. Intravenous loading of azathioprine in IBD does not affect the time to onset of its therapeutic action. 6-TGN in peripheral blood reaches a steady state with oral MP treatment by about 4 weeks, which is well before its pharmacodynamics action. 6-TG effects a 6-TGN-steady state more rapidly, which is likely because the conversion of 6-TG to active drug is not rate-limited by IMPDH.

Figure 7F:
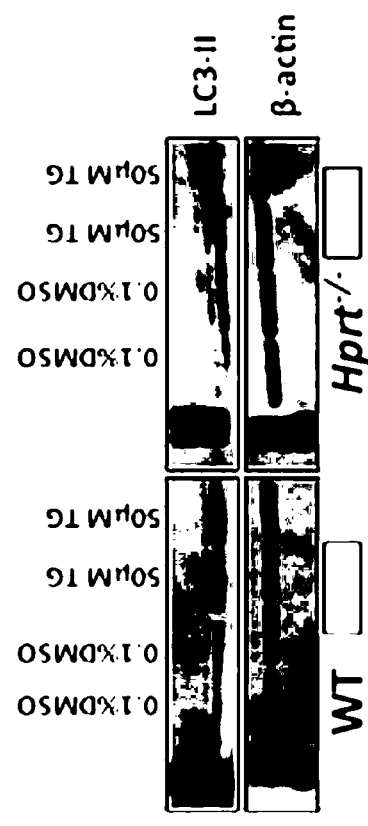
Figure 7F:
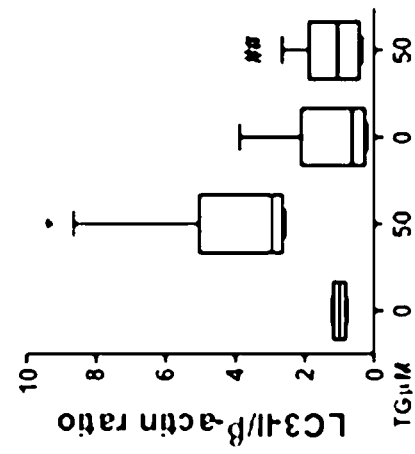

Without being bound by the theory, it is believed that the rapidity of the pharmacodynamic effect of gavaged 6-TG in the murine models is due to local actions of 6-TG that reaches the inflamed distal intestine in the murine models to enhance mucosal barrier function, as well as to enhance innate immune function. This is supported by the rapid local improvement in colitis with intra-rectal 6-TG. The peak gastric-anus transit time in mice is reported to be less than 7 hours, and gavaged 6-TG was demonstrated in faeces [Figure (6C)]. In vitro, 6-TG also improved bulk autophagy handling of bacteria (FIG. 7). 6-TG induces autophagic flux relatively rapidly in both epithelial and macrophages cell lines as well as primary fibroblasts, and that there is an augmented restriction of intracellular bacterial replication through an increase in anti-bacterial autophagy (FIGS. 7A-7F). The effect was due to 6-TGN (or a related metabolite) because this effect was Hprt-dependent (FIG. 7F). These data, i.e. the 6-TG-enhanced bactericidal function, the effect of 6-TG on leukocyte subsets, and the improvement in RaW murine colitis with 6-TG, are in agreement with the recent report which showed that RAC1 inhibition could boost innate immunity (see Parikh K, Zhou L, Somasundaram R, et al. Suppression of p21Rac signaling and increased innate immunity mediate remission in Crohn's disease. *Sci Transl Med* 2014; 6:233-53). Compared to the loading of circulating effector lymphocytes with 6-TGN, the induction of remission in IBD could occur more rapidly via enhanced epithelial barrier and innate immune function through the local conversion of 6-TG by mucosal or microbial HPRT to intracellular mucosal thioGTP. This could be clinically relevant for the treatment of both Crohn's and ulcerative colitis.

Figure 12:
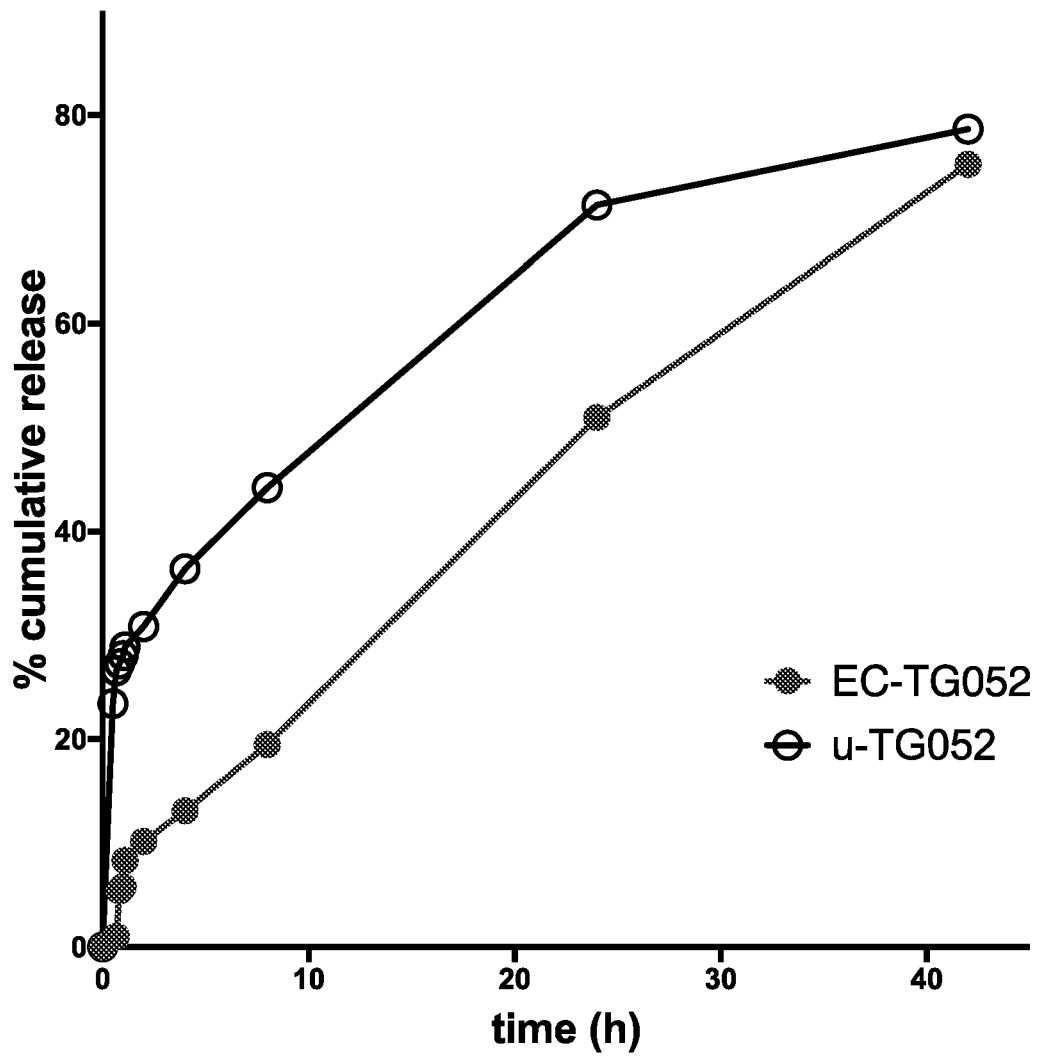
FIG. 12 shows a graphical representation of the percentage cumulative release from the tablet of Formulation 9 (T052/u-TG052) over 42 hours, together with a percentage cumulative release for Formulation 12 (an enterically coated version of the tablet of Formulation 9, EC-TG052) over the same period.
Figure 13:
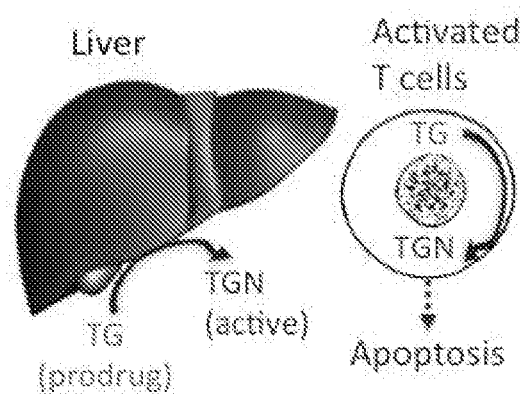
FIG. 13 shows a diagrammatic illustration of the currently accepted paradigm of systemic conversion of 6-TG to the active drug.
Figure 14:
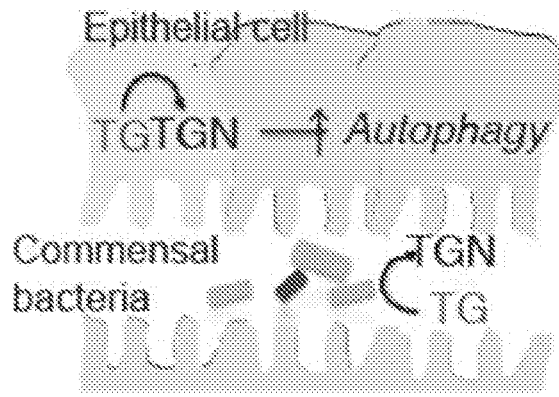
FIG. 14 shows a diagrammatic illustration of the new paradigm for local effects of conversion of 6-TG prodrug to 6-TGTP drug where the 6-TG is metabolized locally by commensal bacteria and/or mucosal cells.

6-TG action is summarized in FIGS. 12 and 13. With reference to FIG. 13, 6-TG entering the portal circulation, is metabolised both by the intestinal mucosa and the liver on first pass circulation, to 6-TGN which has myelosuppressive effects resulting in decreased activated circulating T- and B-lymphocytes as well as decreased myeloid cell numbers. With reference to FIG. 14, 6-TG reaching the colonic lumen has a mild biotic effect on mucosal bacteria and is metabolised by the microbiota to inter alia 6-TGN, thus demonstrating the microbiome converting a pro-drug to an active drug treatment. Mucosa-associated bacteria are increased at sites of inflammation in IBD, and there is diminished mucosal barrier integrity which facilitates increased translocation of bacteria. Therefore, 6-TGN could accumulate in the inflamed distal intestinal mucosa either via local metabolism of 6-TG by the intestinal mucosa, or via both bacterial 6-TGN and autophagy of 6-TGN-laden bacteria. The 6-TGN-augmented autophagy will result in rapid improvement of bacterial handling, decreased immune activation, decreased intestinal inflammation and potentially improved secretory function with restoration of the mucus layer. Unlike 6-MP or azathioprine, 6-TG conversion to active drug by the host or bacteria is not rate limited by IMPDH. Local delivery of 6-TG to sites of intestinal inflammation in IBD would have clinically significant advantages over current oral immunomodulating therapies. In particular, a local delivery of 6-TG could permit a more rapid therapeutic action in IBD without the requirement for circulating CD4+ T-lymphocyte or hepatic conversion to active drug, which would also avoid unwanted adverse effects on liver or haematopoiesis.

Example 8

Preparation of 6-TG Compositions
Reagents

MilliQ purified water, methanol (HPLC grade), propan-2-ol (isopropanol), propylene glycol (PG), sodium hydroxide (NaOH), benzalkonium chloride (BKC), disodium edetate (EDTA), hydrochloric acid (HCl), potassium dihydrogen orthophosphate ($KH_2PO_4$), and sodium phosphate tribasic ($Na_3PO_4.12H_2O$), corn starch, talc, spray dried lactose, magnesium stearate, mannitol, sodium starch glycolate, and methyl-β-cyclodextrin (Me-β-CD) are readily available from commercial sources.

6-TG is commercially available from, for example, Sigma Aldrich or UniWise Hangzhou. Hydroxypropylmethyl celluloses HPMC K100M™ and HPMC K15M™ have a viscosity of about 100,000 cps and about 15 cps respectively. They are commercially available from, for example, Sigma Aldirch or Colorcon.

Eudragit® RS PO is a copolymer of ethyl acrylate, methyl methacrylate and a low content of methacrylic acid ester with quaternary ammonium groups and is available from Evonik Industries.

Eudragit® S100 is a methacrylic acid-methyl methacrylate copolymer and is available from Evonik Industries.

Aerosil™ (fumed silica) is available from Evonik Industries.

Standard solutions, unless described herein, are prepared using standard procedures well known in the art.

10% Propylene glycol solution (PG solution) was prepared by weighing 10 g of propylene glycol (PG) into a 100 mL volumetric flask and the volume was made up using milliQ water.

pH 7.5 buffer was prepared by adding 75 mL of 0.1N HCl to 20 mL of 0.2M tribasic sodium phosphate buffer. The pH was adjusted to 7.5 using 2N HCl and/or 2N NaOH.

0.02M $KH_2PO_4$ was prepared by dissolving 2.72 gm of $KH_2PO_4$ in 900 mL of milliQ water. The pH was adjusted to 3.5 and the volume was made up to 1000 mL. The solution was filtered using a 0.22 μm filter.

Chromatography Equipment and Conditions
    Equipment: Agilent HPLC system
    HPLC Agilent 1260 Infinity system controller
    Hewlett Packard series 1100 autosampler and injector
    Hewlett Packard series 1100 Pump
    Hewlett Packard series 1100 UV detector
Column: Phenomenex Synergi 4μ Hydro-RP, 80A, 250×3.00 mm
Mobile Phase: 10% Methanol in 0.02M $KH_2PO_4$ (pH adjusted to 3.5)
Flow Rate: 0.8 mL/min
Injection Volume: 20 μL UV Detector Wavelength: 341 nm
Retention Time: Approx. 4.7±0.1 mins.

6-TG Enema Formulations

Preparation of Standard Curve and Assay Method

Stock solution: 10 mg of 6-TG and 68 mg of methyl-β-cyclodextrin (Me-β-CD) was accurately weighed and dissolved in 2N NaOH solution. This solution was stirred overnight to obtain dried powder. 50 mL of PG solution was added to the dried powder and the pH was adjusted to 7.6 using 2N HCl and 0.1 N NaOH.

Standard stock solution 1: 5 mL of the stock solution (equivalent to 1 mg of 6-TG) was measured in a 10 mL volumetric flask and volume was made up using 0.1 N NaOH to obtain 100 µg/mL solution.

Standard stock solution 2: 2.5 mL of standard stock solution 1 was measured in 25 mL volumetric flask and the volume was made up using pH 7.5 buffer resulting in 10 µg/mL solution.

Serial dilution of stock solution: 1, 2, 4, 6, and 8 mL of stock solution 3 was measured and made up to 10 mL using pH 7.5 buffer to obtain 1, 2, 4, 6 and 8 µg/mL solution. The standard solutions (1-10 µg/mL) were injected into the HPLC to obtain the standard curve. The standard curve prepared in pH 7.5 over the range of 1-10 µg/mL resulted in a linear curve with the equation of y=125.08x-90.49 and regression coefficient (R2) value of 0.9967.

Drug Assay Method for 20 mg/100 mL 6-TG solution and suspension: 5 mL of 6-TG solution/suspension (equivalent to 1 mg 6-TG) was measured in a 10 mL volumetric flask and volume was made up using 0.1N NaOH and sonicated for 10 mins. 1 mL of solution was measured and made up to 10 mL using pH 7.5 buffer to obtain 10 µg/mL solution which was filtered using 0.22 µm filter and injected into the HPLC to determine the drug concentration.

Drug Assay Method for 80 mg/100 mL 6-TG solution and suspension: 1.25 mL of 6-TG solution/suspension (equivalent to 1 mg 6-TG) was measured in a 5 mL volumetric flask and volume was made up using 0.1N NaOH and sonicated for 10 mins. 0.5 mL of solution was measured and made up to 10 mL using pH 7.5 buffer to obtain 10 µg/mL solution which was filtered using 0.22 µm filter and injected into the HPLC to determine the drug concentration.

Preparation of 6-TG Solution Enema

6-TG has poor aqueous solubility and is only freely soluble in dilute solutions of alkali hydroxides. Conventional formulation methodology using cyclodextrins resulted in hazy solutions with precipitation of 6-TG. To overcome this problem, Methyl-β-CD and 6-TG were dissolved in 2N NaOH solution to obtain a clear solution. This solution was then evaporated at 50° C. overnight to form a complex of Methyl-β-CD and 6-TG as a dry powder. Reconstitution of this powder resulted in a clear solution.

6-TG Solutions

Two strengths of enema solution—20 mg/100 mL and 80 mg/100 mL were prepared.

TABLE 1

Formulation of 6-TG 20 mg100 mL solution
20 mg/100 mL 6-TG Solution

| No. | Ingredients | Role of Ingredient | FDA Permissible limit | Amount/100 mL |
|---|---|---|---|---|
| 1 | 6-TG | Active pharmaceutical ingredient | N/A | 20 mg |
| 2 | Me-β-CD | Solubility enhancer | 0.4% (limit in i.v. infusion) | 157.2 mg |
| 3 | BKC | Preservative | 0.025% (ophthalmic ointment) | 25 mg |
| 4 | EDTA | Preservative | 0.1% (ophthalmic drops) | 100 mg |
| 5 | 2N NaOH | Drug solubiliser | N/A | q.s. |
| 6 | PG Solution | Solvent, Viscosity enhancer | 10% (enema suspension) | q.s. 100 mL |

TABLE 2

Formulation of 6-TG 80 mg/100 mL solution
80 mg/100 mL 6-TG Solution

| No. | Ingredients | Role of Ingredient | FDA Permissible limit | Amount/100 mL |
|---|---|---|---|---|
| 1 | 6-TG | Active pharmaceutical ingredient | N/A | 80 mg |
| 2 | Me-β-CD | Solubility enhancer | 0.4% (limit in i.v. infusion) | 314.4 mg |
| 3 | BKC | Preservative | 0.025% (ophthalmic ointment) | 25 mg |
| 4 | EDTA | Preservative | 0.1% (ophthalmic drops) | 100 mg |
| 5 | 2N NaOH | Drug solubiliser | N/A | q.s. |
| 6 | PG Solution | Solvent, Viscosity enhancer | 10% (enema suspension) | q.s. 100 mL |

Method of Preparation of 6-TG Solutions

6-TG solutions were prepared using complexation technique using Methyl-β-cyclodextrin (Me-β-CD) as the solubilizing agent as described above. The method of preparation for both strengths of 6-TG solutions is as follows:

A) 6-TG and Me-β-CD were weighed in 250 mL glass beaker.

B) Sufficient quantity of 2N NaOH was added to the mixture of step A to obtain a clear solution. The weight of 2N NaOH required was noted.

C) The solution obtained from step B was stirred overnight at 50° C. to give a dry powder complex.

D) 90 mL of PG solution was added to the dry complex to give a clear solution. The BKC and EDTA were added to this solution and the pH was adjusted to 7.7 using NaOH/HCl.

E) The volume was made up to 100 mL using PG solution in 100 mL volumetric flask.

6-TG Enema Suspensions

Two strengths of enema suspension—20 mg/100 mL and 80 mg/100 mL were prepared.

TABLE 3

Formulation of 6-TG 20 mg/100 mL suspension
20 mg/100 mL 6-TG Suspension

| No. | Ingredients | Role of Ingredient | FDA Permissible limit | Amount/100 mL |
|---|---|---|---|---|
| 1 | 6-TG | Active pharmaceutical ingredient | N/A | 20 mg |
| 2 | BKC | Preservative | 0.025% (ophthalmic ointment) | 25 mg |
| 3 | EDTA | Preservative | 0.1% (ophthalmic drops) | 100 mg |
| 4 | PG Solution | Solvent, Viscosity enhancer | 10% (enema suspension) | q.s. 100 mL |

TABLE 4

Formulation of 6-TG 80 mg/100 mL suspension
80 mg/100 mL 6-TG Suspension

| No. | Ingredients | Role of Ingredient | FDA Permissible limit | Amount/100 mL |
|---|---|---|---|---|
| 1 | 6-TG | Active pharmaceutical ingredient | N/A | 80 mg |
| 2 | BKC | Preservative | 0.025% (ophthalmic ointment) | 25 mg |
| 3 | EDTA | Preservative | 0.1% (ophthalmic drops) | 100 mg |
| 4 | PG Solution | Solvent, Viscosity enhancer | 10% (enema suspension) | q.s. 100 mL |

Method of Preparation

The method of preparation for both strengths of 6-TG enema suspensions is as follows:

A) The 6-TG accurately weighed and was added to 250 mL glass beaker containing 90 mL of PG solution.
B) BKC and EDTA were added to the mixture of step A under stirring.
C) The pH was adjusted to 7.7 using NaOH/HCl and the suspension was stirred overnight.
D) The volume was made up to 100 mL using PG solution in 100 mL volumetric flask.

The 6-TG enema solutions and suspensions were analysed for physical appearance, pH, resuspendability and assay (as per method described above Preparation Of Standard Curve And Assay Method). The 6-TG solutions and suspensions (20 mg/100 mL and 80 mg/100 mL) were placed on accelerated stability studies at 40° C./75% RH condition. The stability data for 6-TG solutions and suspensions (20 mg/100 mL and 80 mg/100 mL) are tabulated as follows in Table 5:

TABLE 5

Stability data of 6-TG solutions and suspensions

| | Time (mins) | 20 mg/100 mL Suspension | 20 mg/100 mL Solution | 80 mg/100 mL Suspension | 80 mg/100 mL Solution |
|---|---|---|---|---|---|
| Physical Appearance | 0 | Deflocculated suspension | Clear solution | Deflocculated suspension | Clear solution |
| | 1 | Deflocculated suspension | Clear solution | Deflocculated suspension | Slight precipitation |
| | 2 | | | | |
| | 3 | | | | |
| | 6 | | | | |
| pH | 0 | 7.7 | 7.7 | 7.7 | 7.7 |
| | 1 | 7.4 | 8.8 | 7.5 | 8.7 |
| | 2 | 7.4 | 9.3 | 7.5 | 8.9 |
| | 3 | 7.4 | 9.4 | 7.5 | 9.2 |
| | 6 | 7.4 | 9.4 | 7.9 | 9.2 |
| Resuspendability (Number of inversions) | 0 | 4 | N/A | 6 | N/A |
| | 1 | 4 | N/A | 6 | N/A |
| | 2 | 4 | N/A | 6 | N/A |
| | 3 | 4 | N/A | 6 | N/A |
| | 6 | 4 | N/A | 7 | N/A |
| Assay | 0 | 108.11% | 88.56% | 107.3% | 91.28% |
| | 1 | 98.5% | 73.8% | 107.0% | 85.2% |
| | 2 | 101.8% | 80.45% | 99.15% | 69.87% |
| | 3 | 95.11% | 77.19% | 97.26% | 85.94% |
| | 6 | 97.16% | 70.32% | 96.71% | 83.71% |

The stability data shows, that at the end of 6 months at accelerated conditions, suspensions showed good yield as compared to solution at both the strengths (20 mg/100 mL and 80 mg/100 mL).

6-TG Extended Release Tablets
Preparation of Standard Curve and Assay Method
UV Analysis:
Stock solution: 6-TG (20 mg) was transferred to a 10 mL volumetric flask and dissolved in 4 mL of 2N NaOH solution. The volume was made up using pH 7.5 buffer. Standard stock solution 1: 2.5 mL of the stock solution was measured in a 10 mL volumetric flask and the volume was made up using pH 7.5 buffer to obtain 500 µg/mL solution. Standard stock solution 2: 1 mL of the stock solution was measured in a 10 mL volumetric flask and volume was made up using pH 7.5 buffer to obtain 50 µg/mL solution.
Standard stock solution 3: 5 mL of the stock solution was measured in a 25 mL volumetric flask and volume was made up using pH 7.5 buffer to obtain 10 µg/mL solution.
Serial dilution of standard stock solution 3: 1, 2, 3, 4, 6 and 8 mL of standard stock solution 3 was measured and made up to 10 mL using pH 7.5 buffer to obtain 1, 2, 3, 4, 6 and 8 µg/mL solution. The standard solutions (1-8 µg/mL) were analysed on a UV-Vis spectrometer to obtain the standard curve.
The standard curve prepared in pH 7.5 over the range of 1-8 µg/mL resulted in a linear curve with the equation of y=0.1182x−0.0063 and regression coefficient (R2) value of 0.9997.
HPLC Analysis:
Stock solution: An accurately weighed quantity of TG (20 mg) was transferred in 10 mL volumetric flask and dissolved in 4 mL of 2N NaOH solution. The volume was made up using pH 7.5 buffer.
Standard stock solution 1: 2.5 mL of the stock solution was measured in a 10 mL volumetric flask and volume was made up using pH 7.5 buffer to obtain 500 µg/mL solution.
Standard stock solution 2: 2.5 mL of the stock solution was measured in a 25 mL volumetric flask and volume was made up using pH 7.5 buffer to obtain 50 µg/mL solution.
Standard stock solution 3: 10 mL of the stock solution was measured in a 50 mL volumetric flask and volume was made up using pH 7.5 buffer to obtain 10 µg/mL solution.
Serial dilution of standard stock solution 3: 1, 2, 3, 4, 6, 8 and 10 mL of standard stock solution 3 was measured and made up to 10 mL using pH 7.5 buffer to obtain 1, 2, 3, 4, 6, 8 and 10 µg/mL solution. The standard solutions (1-10 µg/mL) were analysed by HPLC to obtain the standard curve.
The standard curve prepared in pH 7.5 over the range of 0-10 µg/mL resulted in a linear curve with the equation of y=166.04x−56.27 and regression coefficient (R2) value of 0.9968.

The tablets were prepared by direct compression (DC), or wet granulation (WG). Direct compression technique involves mixing of the active ingredient and excipients followed by punching into tablets. Wet granulation is a process of using a liquid binder to lightly agglomerate the powder mixture of drug and excipients resulting in dough like material. This material was screened through mesh to obtain granules. These granules were dried and again passed through a screen of smaller size than the one used for the wet mass to create granules of uniform size. Lubricant mixture was added to the dried granules and the mixture was punched to obtain tablets.

Commercially available 6-TG tablets are available as 20 mg tablets (Thiosix™) and 40 mg (Lanvis™, Tabloid™). These tablets are considered to be "immediate release" and release all of the 6-TG within 3 to 4 hours of oral administration in the stomach.

Extended release tablets comprising 20 mg of 6-TG were prepared using a wet granulation technique (Formulations 1, and 3-11) or a direct compression technique (Formulation 2). Tablets were punched using a Manesty E2 single punch tablet press with an 8 mm convex punch (Formulations 1-4), or a 6.5 mm convex punch (Formulations 5-11).

Formulation 1 (T008)

| | 6-TG Tablet T008 (WG) | |
|---|---|---|
| | Ingredients | Amount (mg) |
| 1 | 6-TG | 20 |
| 2 | HPMC (K100M) | 20 |
| 3 | Corn starch | 155 |
| 4 | Talc | 5 |
| | Total | 200 |

Formulation 1 was prepared using a wet granulation technique.
A) Ingredients 1-3 were sifted through 40# sieve.
B) A mixture of propan-2-ol and water was added drop wise to the mixture of step A to achieve uniform and consistent dough.
C) The dough from step B was passed through 20# sieve and dried at 60° C. for 15 minutes.
D) The moisture content should be between 0.5-1%.
E) The dried granules were passed through 40# sieve.
F) Ingredient 4 was sieved through 40# sieve and added to the granules of step E.

Formulation 2 (T012)

| | 6-TG Tablet T012 (DC) | |
|---|---|---|
| | Ingredients | Amount (mg) |
| 1 | 6-TG | 20 |
| 2 | HPMC(K15M) | 60 |
| 3 | Spray dried lactose | 118 |
| 4 | Magnesium stearate | 1 |
| 5 | Talc powder | 1 |
| | Total | 200 |

Formulation 2 was prepared using a direct compression technique.
A) Ingredients 1-3 were sifted through 40# sieve.
B) The sieved blend was mixed thoroughly for 10 mins in a plastic bag.
C) Ingredients 4 and 5 were sieved through 40# sieve and added to the mixture of step B.
D) The blend was mixed thoroughly for 5 mins in a plastic bag.

Formulation 3 (T025)

| | 6-TG Tablet T025 (WG) | |
|---|---|---|
| | Ingredients | Amount (mg) |
| 1 | 6-TG | 20 |
| 2 | HPMC (K100M) | 20 |
| 3 | Mannitol | 58 |
| 4 | Corn starch | 100 |
| 5 | Aerosil ™ | 2 |
| | Total | 200 |

Formulation 3 was prepared by a wet granulation technique.
A) Ingredients 1-4 were sifted through 40# sieve.
B) A mixture of propan-2-ol and water was added drop wise to the mixture of step A to achieve a uniform and consistent dough.

C) The dough from step B was passed through 20# sieve and dried at 60° C. for 15 minutes.

D) The moisture content should be between 0.5-1%.

E) The dried granules were passed through 40# sieve.

F) Ingredient 5 was sieved through 40# sieve and added to the product of step E.

Formulation 4 (T038)

| 6-TG Tablet T038 (WG) | | |
| --- | --- | --- |
| | Ingredients | Amount (mg) |
| 1 | 6-TG | 20 |
| 2 | HPMC (K100M) | 10 |
| 3 | Eudragit RSPO | 40 |
| 4 | Sodium lauryl sulphate | 30 |
| 5 | Corn starch | 86 |
| 6 | Sodium starch glycolate | 10 |
| 7 | Aerosil ™ | 2 |
| 8 | Talc | 2 |
| | Total | 400 |

Formulation 4 was prepared using a wet granulation technique.

A) Ingredients 1, 2, 4, 5, 6 were sifted through 40# sieve.

B) A mixture of propan-2-ol and water was added drop wise to the mixture of step A to achieve a uniform and consistent dough. (6.83 mL of propan-2-ol and 16.33 mL of water) C) The dough from step B was passed through 20# sieve and dried at 60° C. for 15 minutes.

D) Ideally the moisture content should be between 0.5-1.

E) The dried granules were passed through 40# sieve.

F) Ingredients 3, 7, 8 were sieved through 40# sieve and added to the mixture of step E Formulation 5 (T047)

| 6-TG Tablet T047 (WG) | | |
| --- | --- | --- |
| | Ingredients | Amount (mg) |
| 1 | 6-TG | 20 |
| 2 | HPMC (K100M) | 5 |
| 3 | Corn starch | 82.5 |
| 4 | Magnesium stearate | 2.5 |
| | Total | 110 |

Formulation 6 (T048)

| 6-TG Tablet T048 (WG) | | |
| --- | --- | --- |
| | Ingredients | Amount (mg) |
| 1 | 6-TG | 20 |
| 2 | HPMC (K100M) | 5 |
| 3 | Spray dried lactose | 55 |
| 4 | Corn starch | 10 |
| 5 | Starch paste (10% w/w) | q.s. |
| 6 | Magnesium stearate | 2 |
| 7 | Aerosil ™ | 2 |
| | Total | 100 |

Formulation 7 (T049)

| 6-TG Tablet T049 (WG) | | |
| --- | --- | --- |
| | Ingredients | Amount (mg) |
| 1 | 6-TG | 20 |
| 2 | HPMC (K15M) | 10 |
| 3 | Spray dried lactose | 66 |
| 4 | Magnesium stearate | 2 |
| 5 | Talc | 2 |
| | Total | 100 |

Formulation 8 (T050)

| 6-TG Tablet T050 (WG) | | |
| --- | --- | --- |
| | Ingredients | Amount (mg) |
| 1 | 6-TG | 20 |
| 2 | HPMC (K100M) | 5 |
| 3 | Spray dried lactose | 55 |
| 4 | Corn starch | 14 |
| 5 | Magnesium stearate | 2 |
| 6 | Talc | 2 |
| | Total | 98 |

Formulation 9 (T052)

| 6-TG Tablet T052 (WG) | | |
| --- | --- | --- |
| | Ingredients | Amount (mg) |
| 1 | 6-TG | 20 |
| 2 | HPMC (K100M) | 2.5 |
| 3 | Corn starch | 75 |
| 4 | Magnesium stearate | 2.5 |
| | Total | 100 |

Formulation 10 (T053)

| 6-TG Tablet T053 (WG) | | |
| --- | --- | --- |
| | Ingredients | Amount (mg) |
| 1 | 6-TG | 20 |
| 2 | HPMC (K15M) | 5 |
| 3 | Spray dried lactose | 71 |
| 4 | Magnesium stearate | 2 |
| 5 | Talc | 2 |
| | Total | 100 |

Formulation 11 (T054)

| 6-TG Tablet T054 (WG) | | |
| --- | --- | --- |
| | Ingredients | Amount (mg) |
| 1 | 6-TG | 20 |
| 2 | HPMC (K100M) | 2.5 |
| 3 | Spray dried lactose | 63.5 |
| 4 | Corn starch | 10 |
| 5 | Magnesium stearate | 2 |
| 6 | Aerosil ™ | 2 |
| | Total | 100 |

Formulations 5 to 11 were prepared by wet granulation methods analogous to those described above for Formulations 1, 3 and 4.

Formulation 12 (EC-TG052)

An enteric coated version of the tablet of Formulation 9 (T052) was prepared by applying a polymeric enteric coating to the tablet. Tablets containing 20 mg of 6-TG (T052), each weighing 100 mg, were dipped in a 4% w/v solution of Eudragit S100 (Evonik Laboratories) in a 1:1 mixture of propan-2-ol/acetone. The coated tablets were then air dried. The dipping and drying process was repeated twice more to give enteric coated tablets comprising 20 mg of 6-TG (EC-TG052).

Tablet Characterisation

Hardness

Tablet hardness was measured using Erweka TBH20 apparatus.

Disintegration Test

Disintegration studies for the 6-TG tablets were conducted using Erweka ZT124 apparatus.

Friability

Friability studies were conducted using Erweka TAR220 apparatus. 10 tablets were weighed and placed in the friability drum at 100 rpm. After the test, the tablets were collected and observed for any physical damage. The tablets were weighed again and the % friability was determined.

Dissolution Studies

Drug release studies were conducted using Varian VK7000 apparatus (USP General Chapter <711> Dissolution, USP Dissolution Apparatus 2-Paddle). The dissolution studies were conducted in both gastric and intestinal environment to mimic the actual physiological conditions. The release rate was conducted using USP-II apparatus (paddle) at 50 rpm. The tablet was immersed in 750 mL of 0.1 N HCl at 37° C.

After 1 hr of operation, 200 mL of tribasic sodium phosphate buffer that has been equilibrated at 37° C. was added to the vessel. The pH was adjusted to 7.5, if necessary using 2N NaOH or 2N HCl. The operation of adding the buffer and adjusting the pH was completed within 5 mins. The dissolution apparatus was continued for another 48 hrs. An aliquot of 5 mL was withdrawn for analysis at fixed time intervals (after 1 hr in 0.1N HCl, 1, 2, 4, 8, 24 and 48 hrs after adjusting the pH to 7.5). An equivalent volume of fresh pH 7.5 buffer solution was adjusted after each aliquot withdrawal (except for 0.1N HCl aliquot). Each sample was analysed by UV spectroscopy and HPLC. Results are summarized graphically in FIGS. 8A and 8B.

Drug Assay Method 5 tablets were crushed to powder using a mortar and pestle. Powder equivalent to the average weight of 5 tablets was weighed and transferred to a 200 mL volumetric flask. Approximately 150 mL of 0.5N NaOH was added to the volumetric flask and this was subjected to sonication for 20 mins.

The volume was made up using 0.5N NaOH. A small quantity of aliquot was filtered. 0.5 mL of the filtered aliquot was taken out in a 10 mL volumetric flask and the volume was made up to pH 7.5 and analysed by UV spectrometer and HPLC.

According to the US Pharmacopoeia, 6-TG tablets should not contain less than 93.0% and more than 107.0% of the labelled amount of 6-thioguanine.

Results

6-TG Release Rates

Figure 10:
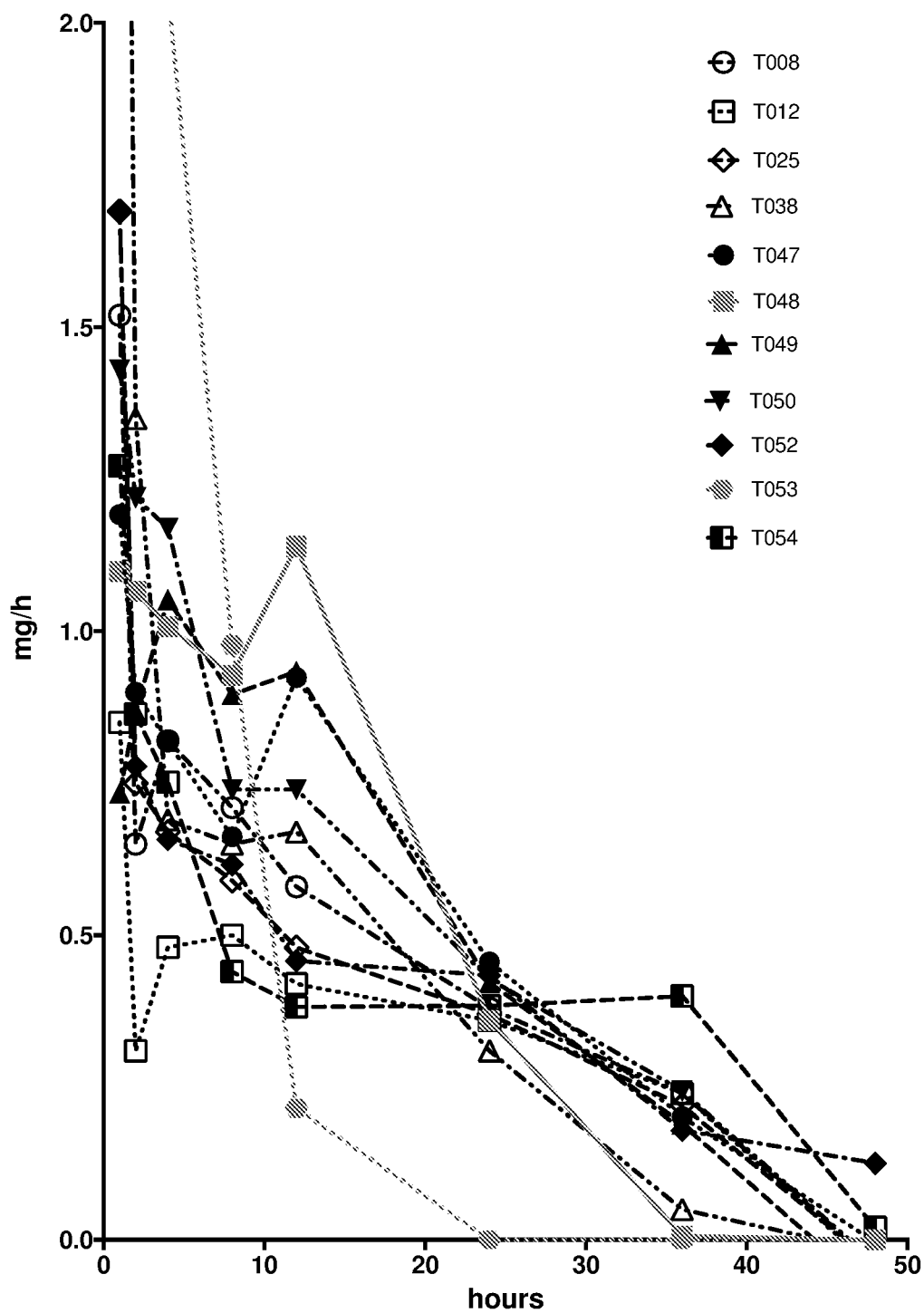
FIG. 10 shows a graphical representation of the 6-TG release rate from 6-TG tablets of Formulations 1 to 11 at pH 7.5.

Release rates for the tablet formulations 1 to 11 at pH 7.5 are summarized in graphical form in FIG. 10.

Figure 9:
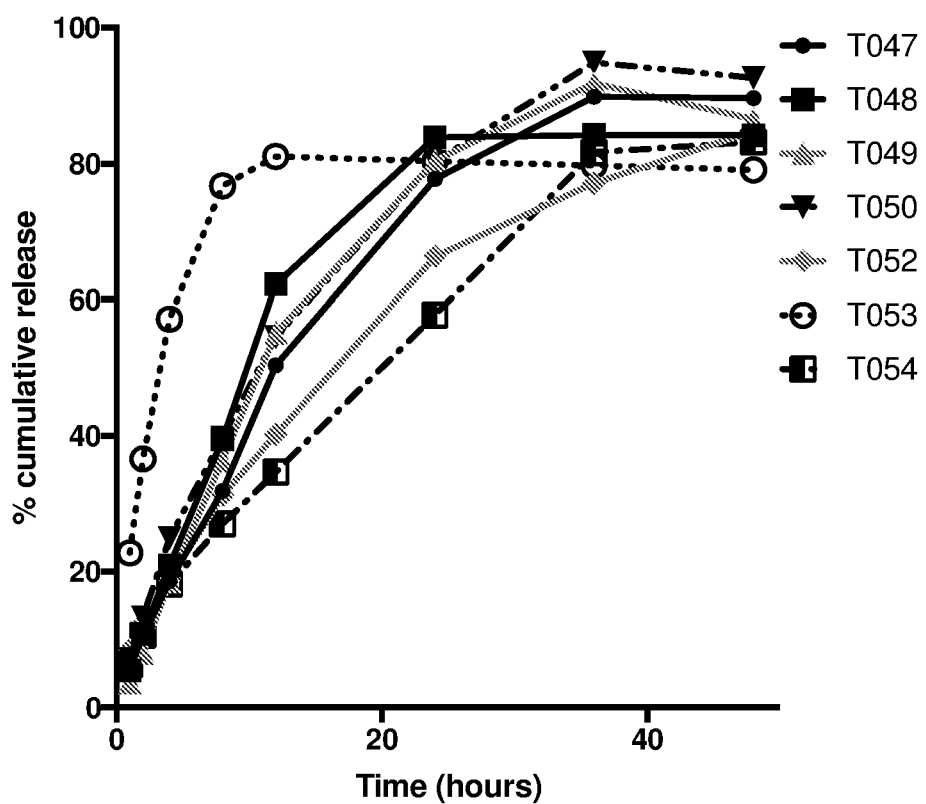
FIG. 9 shows a graphical representation of the percentage cumulative release of 6-TG from 6-TG tablets of Formulations 5 to 11 at pH 7.5 over 48 hours.

Percentage cumulative release rates for the Formulations 1 to 11 are summarized below in Table 6. FIG. 9 shows graphical representations for the percentage cumulative release of 6-TG from the tablets of Formulations 5 to 11 at pH 7.5 over 48 hours.

TABLE 6

Cumulative Release Rates for Formulations 1 to 11
Percentage Cumulative Release

| Time (Hours) | 1 T008 | 2 T012 | 3 T025 | 4 T038 | 5 T047 | 6 T048 | 7 T049 | 8 T050 | 9 T052 | 10 T053 | 11 T054 |
|---|---|---|---|---|---|---|---|---|---|---|---|
| 1 | 7.59 | 4.25 | 8.43 | 20.07 | 5.69 | 5.48 | 3.67 | 7.15 | 8.45 | 22.79 | 6.36 |
| 2 | 10.86 | 5.82 | 12.17 | 26.83 | 10.46 | 10.81 | 8.01 | 13.25 | 12.34 | 36.62 | 10.68 |
| 4 | 19.08 | 10.64 | 18.90 | 33.75 | 18.64 | 20.90 | 18.53 | 24.96 | 18.92 | 57.17 | 18.21 |
| 8 | 33.28 | 20.59 | 30.67 | 46.75 | 31.90 | 39.48 | 36.43 | 39.78 | 31.18 | 76.72 | 27.00 |
| 12 | 44.93 | 28.94 | 43.36 | 60.09 | 50.38 | 62.26 | 55.12 | 54.59 | 40.24 | 81.04 | 34.64 |
| 24 | 67.81 | 50.69 | 62.85 | 78.80 | 77.73 | 83.85 | 80.39 | 80.28 | 66.33 | 80.34 | 57.73 |
| 36 | 82.17 | 65.31 | 76.28 | 81.91 | 89.83 | 84.21 | 91.82 | 94.86 | 77.14 | 79.71 | 81.68 |
| 48 | 92.66 | 78.17 | 85.48 | 86.83 | 89.62 | 84.16 | 86.51 | 92.62 | 84.75 | 79.05 | 83.17 |

The cumulative percentage release for the tablet of Formulation 9 (T052) over 48 hours is summarized in graphical form in FIG. 11 (solid line). FIG. 11 also shows estimated percentage cumulative release over 48 hours for an enterically coated version of Formulation 9 (broken line).

The cumulative percentage release for the enteric coated tablet of Formulation 12 (EC-TG052) was determined experimentally. Tablet EC-TG052 was incubated in gastric simulation fluid for 1 hour. The fluid was then buffered to pH 7 to mimic intestinal fluid. The release of 6-TG from the tablet was measured over 42 hours. For comparison, the cumulative percentage release was determined for the uncoated version of the tablet (Formulation 9, T052/u-TG052). The release profile of EC-TG052 was compared with that of the uncoated version (u-TG052) and the results are summarized graphically in FIG. 12. FIG. 12 shows that the enteric coated tablet substantially inhibits release of 6-TG in the simulated gastric fluid.

The 6-TG tablets of Formulations 1 to 4 were placed on accelerated stability studies at 40° C./75% RH conditions for the time period of 1, 2, 3 and 6 months. The 6-TG tablets were analyzed for physical appearance, weight uniformity, hardness, friability, disintegration studies, drug release and assay.

The stability data for the 6-TG tablet formulations 1 to 11 are summarized in Table 7:

TABLE 7

Stability Data for 6-TG Tablets

| | Time, M | T008 (WG) | T012 (DC) | T025 (WG) | T038 (WG) |
|---|---|---|---|---|---|
| Physical appearance | 0<br>1<br>2<br>3<br>6 | Pale yellow colored tablet | Pale yellow colored tablet | Pale yellow colored tablet, Slight rough edges | Pale yellow colored tablet. Slightly rough surface |
| Weight uniformity, (avg. ± SD) mg | 0<br>1<br>2<br>3<br>6 | 201.4 ± 1.89<br>201.7 ± 2.19<br>200.5 ± 2.18<br>200.2 ± 1.70<br>200.2 ± 1.51 | 200.4 ± 1.73<br>200.7 ± 1.95<br>200.2 ± 1.65<br>200.8 ± 1.53<br>201.8 ± 1.30 | 199.6 ± 1.18<br>200.1 ± 1.46<br>200.2 ± 2.09<br>200.5 ± 1.60<br>199.6 ± 2.18 | 201.5 ± 2.59<br>201.3 ± 1.32<br>202.3 ± 1.63<br>201.8 ± 1.30<br>201.6 ± 0.80 |
| Hardness, N | 0<br>1<br>2<br>3<br>6 | 65-75<br>60-65<br>60-70<br>55-65<br>60-70 | 50-60<br>50-65<br>60-70<br>60-70<br>60-70 | 60-70<br>80-95<br>80-90<br>70-80<br>80-90 | 30-40<br>40-55<br>30-40<br>50-60<br>60-70 |
| Friability | 0<br>1<br>2<br>3<br>6 | 0.21%<br>0.1%<br>0.07%<br>0.14%<br>0.58% | 0.19%<br>0.1%<br>0.16%<br>0.15%<br>0.65% | 0.21%<br>0.12%<br>0.06%<br>0.14%<br>0.48% | 1.09%<br>0.59%<br>0.61%<br>0.56%<br>1.43% |
| Disintegration Time (0.1N HCl, 1 h) | 0<br>1<br>2<br>3<br>6 | Intact<br>Intact<br>Intact<br>Intact<br>Intact | Intact<br>Intact<br>Intact<br>Intact<br>Intact | Intact<br>Intact<br>Intact<br>Intact<br>Intact | Intact<br>Intact<br>Intact<br>Intact<br>Intact |
| Assay | 0<br>1<br>2<br>3<br>6 | 97.67%<br>97.59%<br>95.05%<br>98.14%<br>97.40% | 87.72%<br>100.25%<br>93.76%<br>88.81%<br>91.55% | 101.86%<br>108.46%<br>96.44%<br>93.70%<br>99.73% | 95.87%<br>89.08%<br>92.64%<br>97.34%<br>98.45% |

Figure 8A:
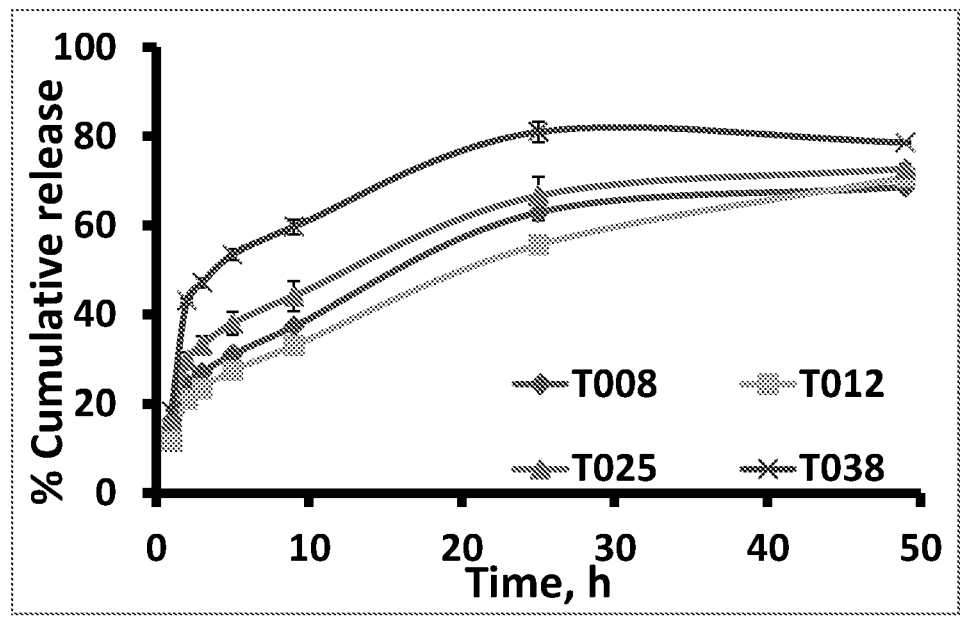
FIGS. 8A and 8B show graphical representations of the percentage 6-TG cumulative release for 6-TG tablet formulations 1 to 4. These dissolution studies were conducted at pH 1-2 for 1 hour, and then at pH 7.5 for 48 hours. Data were obtained at an initial stage prior to conducting stability studies of the 6-TG tablets at 40° C./75% RH (relative humidity) conditions (FIG. 8A). The percentage 6-TG cumulative release was determined for 6-TG tablets after 6 months of stability testing at 40° C./75% RH conditions (FIG. 8B).
Figure 8B:
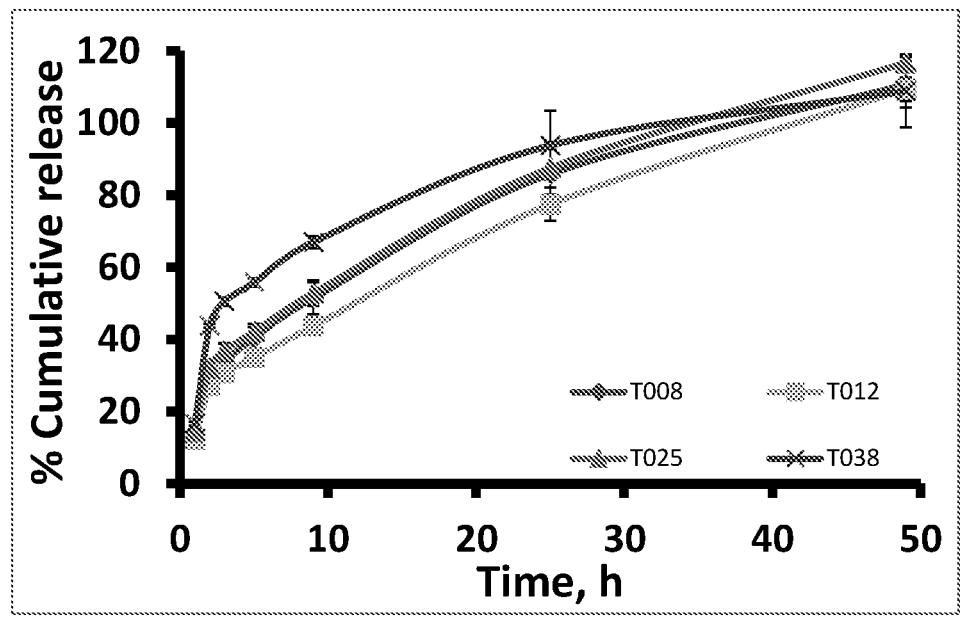

FIGS. 8A and 8B show the cumulative release data for the tablets of formulations 1 to 4 (T008, T012, T025 and T038) at the initial stage, and after 6 months of accelerated aging conditions.

These data show that at the end of 6 months under accelerated conditions, all the tablets showed little variation in comparison to time zero for the physical parameters. However, the data for the 6-TG tablet of Formulation 2 showed a greater deviation from time zero than the 6-TG tablets of Formulations 1, 3 and 4. The lower assay for the tablet of Formula 2 could be attributed to its method of preparation, i.e., direct compression, which may have led to inefficient mixing or sticking of drug powder to the wall during mixing. In the wet granulation method, the active component (6-TG) forms a homogenous mixture due to efficient mixing with excipients in the presence of solvent. Thus, it could be concluded that the 6-TG tablets prepared by the wet granulation method (i.e., formulations 1, 3 and 4) are able to release 6-TG in controlled manner and reach release of about 80% of 6-TG content by the end of 24 h leading to effective drug availability at colon region.

Any document cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

Many modifications will be apparent to those skilled in the art without departing from the scope of the present invention.

What is claimed is:

1. A pharmaceutical composition comprising 6-TG and a homogeneous erodible hydrophilic polymer matrix, wherein the composition is formulated for oral administration and provides release of at least 35% of the 6-TG in vitro at about pH 6 to about pH 7.5 after approximately 12 hours.

2. A pharmaceutical composition according to claim 1 in solid dosage form.

3. A pharmaceutical composition according to claim 1 comprising an enteric coating.

4. A pharmaceutical composition according to claim 1 wherein the composition is adapted to provide substantially zero order kinetics of 6-TG release between approximately 12 hours and 24 hours from oral administration.

5. A pharmaceutical composition according to claim 1 wherein the composition provides release of at least 60% of the 6-TG in vitro at about pH 6 to about pH 7.5 after approximately 12 hours.

6. A pharmaceutical composition according to claim 1, wherein the composition is adapted to avoid substantial systemic concentrations of 6-TG.

7. The pharmaceutical composition according to claim 1, wherein the composition provides release of at least 50%, 55%, 60%, 65%, 70%, 75%, 80%, 85%, 90% or 95% of the 6-TG in vitro at about pH 6 to about pH 7.5 after approximately 12 hours.

8. A pharmaceutical composition according to claim 1 in microparticulate dosage form.

9. The pharmaceutical composition according to claim 1 wherein the composition provides release of at least 45% of the 6-TG in vitro at about pH 6 to about pH 7.5 after approximately 12 hours.

10. A pharmaceutical composition according to claim 1, wherein the pH is about 6.

11. A pharmaceutical composition according to claim 1, wherein the pH is about 7.5.

12. A pharmaceutical composition according to claim 1, wherein the homogeneous erodible hydrophilic polymer matrix comprises polyethylene oxides.

13. A pharmaceutical composition according to claim 1, wherein the homogeneous erodible hydrophilic polymer matrix comprises both a hydrophilic and a hydrophobic polymer.

14. A pharmaceutical composition according to claim 13, wherein the homogeneous erodible hydrophilic polymer matrix comprises ethyl cellulose.

15. A pharmaceutical composition according to claim 1, wherein the homogeneous erodible hydrophilic polymer matrix comprises polyethylene oxides and the pharmaceutical composition comprises an enteric coating.

16. A pharmaceutical composition according to claim 1, wherein the homogeneous erodible hydrophilic polymer matrix comprises polyethylene oxides and ethyl cellulose, and the pharmaceutical composition comprises an enteric coating.

* * * * *